(12) United States Patent
Barrows et al.

(10) Patent No.: US 7,597,885 B2
(45) Date of Patent: *Oct. 6, 2009

(54) TISSUE ENGINEERED BIOMIMETIC HAIR FOLLICLE GRAFT

(75) Inventors: Thomas H. Barrows, Austell, GA (US); Stephen A. Cochran, Tucker, GA (US); Bryan Marshall, Atlanta, GA (US)

(73) Assignee: Aderans Research Institute, Inc., Marietta, GA (US)

( * ) Notice: Subject to any disclaimer, the term of this patent is extended or adjusted under 35 U.S.C. 154(b) by 272 days.

This patent is subject to a terminal disclaimer.

(21) Appl. No.: 10/810,518

(22) Filed: Mar. 26, 2004

(65) Prior Publication Data

US 2005/0214344 A1 Sep. 29, 2005

(51) Int. Cl.
*A61K 31/74* (2006.01)
*A01N 63/00* (2006.01)
*A01N 65/00* (2006.01)
*C12N 11/04* (2006.01)

(52) U.S. Cl. ..................... 424/93.7; 435/182
(58) Field of Classification Search .................. None
See application file for complete search history.

(56) References Cited

U.S. PATENT DOCUMENTS

| | | | |
|---|---|---|---|
| 2,946,769 A | 7/1960 | Rose et al. |
| 3,025,323 A | 3/1962 | Rose et al. |
| 3,596,292 A | 8/1971 | Erb et al. |
| 3,966,766 A | 6/1976 | Lehn |
| 4,052,988 A | 10/1977 | Doddi et al. |
| 4,104,195 A | 8/1978 | Ley et al. |
| 4,209,607 A | 6/1980 | Shalaby et al. |
| 4,226,243 A | 10/1980 | Shalaby et al. |
| 4,242,931 A | 1/1981 | Clement |
| 4,343,931 A | 8/1982 | Barrows |
| 4,384,061 A | 5/1983 | Reiter et al. |
| 4,429,080 A | 1/1984 | Casey et al. |
| 4,458,678 A | 7/1984 | Yannas et al. |
| 4,505,266 A | 3/1985 | Yannas et al. |
| 4,529,792 A | 7/1985 | Barrows |
| 4,604,097 A | 8/1986 | Graves, Jr. et al. |
| 4,643,734 A | 2/1987 | Lin |
| 4,719,917 A | 1/1988 | Barrows et al. |
| 4,851,521 A | 7/1989 | della Valle et al. |
| 4,919,664 A | 4/1990 | Oliver et al. |
| 4,947,840 A | 8/1990 | Yannas et al. |
| 5,061,284 A | 10/1991 | Laghi |
| 5,091,173 A | 2/1992 | Buultjens et al. |
| 5,133,739 A | 7/1992 | Bezwada et al. |
| 5,141,522 A | 8/1992 | Landi |
| 5,147,400 A | 9/1992 | Kaplan et al. |
| 5,194,473 A | 3/1993 | Shinoda et al. |
| 5,198,507 A | 3/1993 | Kohn et al. |
| 5,286,837 A | 2/1994 | Barrows et al. |
| 5,393,323 A | 2/1995 | Simmons |
| 5,403,347 A | 4/1995 | Roby et al. |
| 5,415,378 A | 5/1995 | Craven |
| 5,423,778 A | 6/1995 | Eriksson et al. |
| 5,486,593 A | 1/1996 | Tang et al. |
| 5,502,092 A | 3/1996 | Barrows et al. |
| 5,514,378 A | 5/1996 | Mikos et al. |
| 5,522,841 A | 6/1996 | Roby et al. |
| 5,545,208 A | 8/1996 | Wolff et al. |
| 5,556,783 A | 9/1996 | Lavker et al. |
| 5,578,046 A | 11/1996 | Liu et al. |
| 5,599,552 A | 2/1997 | Dunn et al. |
| 5,611,811 A | 3/1997 | Goldberg |
| 5,639,645 A | 6/1997 | Murata |
| 5,661,132 A | 8/1997 | Eriksson et al. |
| 5,667,961 A | 9/1997 | Bernard et al. |
| 5,674,286 A | 10/1997 | D'Alessio et al. |
| 5,677,355 A | 10/1997 | Shalaby et al. |
| 5,690,961 A | 11/1997 | Nguyen |
| 5,697,901 A | 12/1997 | Eriksson |
| 5,697,976 A | 12/1997 | Chesterfield et al. |

(Continued)

FOREIGN PATENT DOCUMENTS

| CA | 2140090 | 8/1995 |
|---|---|---|
| CA | 2199918 | 9/1997 |
| CN | 1594554 | 3/2005 |

(Continued)

OTHER PUBLICATIONS

U.S. Appl. No. 11/107,230, filed Apr. 2005, Barrows.
U.S. Appl. No. 11/203,804, filed Aug. 2005, Barrows.
Arase, S. et al., "Co-culture of human hair follicles and dermal papillae in a collagen matrix," J. Dermatol. (1990) 17:667-676.
Arias, Am and Stewart A. (2002) Molecular Principles of Animal Development Oxford University Press, Oxford University Press, Oxford.

(Continued)

*Primary Examiner*—David M. Naff
*Assistant Examiner*—Deborah K. Ware
(74) *Attorney, Agent, or Firm*—Pabst Patent Group LLP

(57) ABSTRACT

The present invention relates to an improved scaffold which is constructed to mimic the architecture of the native hair follicle. The present invention also relates to the use of specific compositions and methods of manufacture to produce scaffolds that combine biocompatibility with the desired rates of bioabsorption. In another embodiment, the present invention relates to a process for manufacturing a biomimetic hair follicle graft and a method for seeding the graft with cells and implanting the graft into the skin where the growth of a new hair shaft is desired. A further embodiment of the present invention relates to a method for hair multiplication in which cells are multiplied in culture and aliquoted into a multitude of bioabsorbable scaffolds in combination with cultured keratinocytes or other allogenic cells.

19 Claims, 14 Drawing Sheets

U.S. PATENT DOCUMENTS

| | | | |
|---|---|---|---|
| 5,712,169 A | 1/1998 | Bernard et al. | |
| 5,721,049 A | 2/1998 | Marcolongo et al. | |
| 5,723,508 A | 3/1998 | Healey et al. | |
| 5,756,094 A | 5/1998 | Lavker et al. | |
| 5,767,152 A | 6/1998 | Nielsen et al. | |
| 5,770,417 A | 6/1998 | Vacanti et al. | |
| 5,817,120 A | 10/1998 | Rassman | |
| 5,847,012 A | 12/1998 | Shalaby et al. | |
| 5,891,426 A | 4/1999 | Jarrousse et al. | |
| 5,891,558 A * | 4/1999 | Bell et al. | 428/218 |
| 5,898,040 A | 4/1999 | Shalaby et al. | |
| 5,919,893 A | 7/1999 | Roby et al. | |
| 5,939,323 A | 8/1999 | Valentini et al. | |
| 5,945,115 A | 8/1999 | Dunn et al. | |
| 5,989,279 A | 11/1999 | Rassman | |
| 5,993,374 A | 11/1999 | Kick | |
| 5,997,468 A | 12/1999 | Wolff et al. | |
| 5,997,568 A | 12/1999 | Liu | |
| 6,001,378 A | 12/1999 | Desjonqueres | |
| 6,027,744 A | 2/2000 | Vacanti et al. | |
| 6,031,148 A | 2/2000 | Hayes et al. | |
| 6,051,750 A | 4/2000 | Bell | |
| 6,093,200 A | 7/2000 | Liu et al. | |
| 6,120,788 A | 9/2000 | Barrows | |
| 6,147,135 A | 11/2000 | Yuan et al. | |
| 6,159,950 A | 12/2000 | Crystal et al. | |
| 6,303,697 B1 | 10/2001 | Yuan et al. | |
| 6,333,029 B1 | 12/2001 | Vyakarnam et al. | |
| 6,350,284 B1 | 2/2002 | Tormala et al. | |
| 6,365,172 B1 | 4/2002 | Barrows | |
| 6,383,220 B1 | 5/2002 | Van Blitterswijk et al. | |
| 6,423,252 B1 | 7/2002 | Chun et al. | |
| 6,436,424 B1 | 8/2002 | Vogel et al. | |
| 6,474,344 B2 | 11/2002 | Yamada | |
| 6,503,539 B2 | 1/2003 | Gestrelius et al. | |
| 6,511,748 B1 | 1/2003 | Barrows | |
| 6,569,143 B2 | 5/2003 | Alchas et al. | |
| 6,613,798 B1 | 9/2003 | Porter et al. | |
| 6,639,051 B2 | 10/2003 | Wang | |
| 6,660,301 B1 | 12/2003 | Vogel et al. | |
| 6,699,287 B2 | 3/2004 | Son et al. | |
| 6,773,713 B2 | 8/2004 | Bonassar et al. | |
| 6,878,383 B2 | 4/2005 | Boss, Jr. et al. | |
| 6,884,427 B1 | 4/2005 | Barrows | |
| 7,198,641 B2 * | 4/2007 | Barrows | 623/15.11 |
| 2002/0049426 A1 | 4/2002 | Butler et al. | |
| 2002/0083216 A1 | 6/2002 | Hickson et al. | |
| 2002/0090725 A1 * | 7/2002 | Simpson et al. | 435/402 |
| 2002/0172705 A1 | 11/2002 | Murphy et al. | |
| 2002/0193740 A1 | 12/2002 | Alachas et al. | |
| 2002/0193778 A1 | 12/2002 | Alachas et al. | |
| 2002/0197326 A1 | 12/2002 | Vogel et al. | |
| 2003/0009113 A1 | 1/2003 | Olson | |
| 2003/0049839 A1 * | 3/2003 | Romero-Ortega et al. | 435/397 |
| 2003/0072784 A1 | 4/2003 | Williams | |
| 2003/0077311 A1 | 4/2003 | Vyakarnam et al. | |
| 2003/0077823 A1 | 4/2003 | Li et al. | |
| 2003/0134099 A1 | 7/2003 | Barrows | |
| 2003/0147831 A1 | 8/2003 | Marko | |
| 2003/0161815 A1 | 8/2003 | Wolowacz et al. | |
| 2003/0166274 A1 | 9/2003 | Hewitt et al. | |
| 2003/0195625 A1 | 10/2003 | Garcia Castro et al. | |
| 2003/0198646 A1 | 10/2003 | Stenn | |
| 2003/0203003 A1 | 10/2003 | Nelson et al. | |
| 2003/0208138 A1 | 11/2003 | Olson | |
| 2003/0211083 A1 | 11/2003 | Vogel et al. | |
| 2003/0235813 A1 | 12/2003 | Luyten et al. | |
| 2004/0033598 A1 | 2/2004 | Vacanti et al. | |
| 2004/0039438 A1 | 2/2004 | Alt | |
| 2004/0054410 A1 | 3/2004 | Barrows | |
| 2004/0057937 A1 | 3/2004 | Jahoda et al. | |
| 2004/0068284 A1 | 4/2004 | Barrows | |
| 2004/0096514 A1 | 5/2004 | Vogel | |
| 2004/0220589 A1 | 11/2004 | Feller | |
| 2005/0089512 A1 | 4/2005 | Schlotmann et al. | |
| 2005/0106723 A1 | 5/2005 | Hatzfeld et al. | |
| 2005/0147652 A1 | 7/2005 | Atkins et al. | |
| 2005/0233450 A1 | 10/2005 | Goetinck et al. | |
| 2005/0272150 A1 | 12/2005 | Teumer et al. | |
| 2006/0057126 A1 | 3/2006 | Tankovich | |
| 2007/0092496 A1 | 4/2007 | Zheng et al. | |
| 2007/0122387 A1 | 5/2007 | Cochran et al. | |
| 2007/0148138 A1 | 6/2007 | Barrows et al. | |
| 2007/0233038 A1 | 10/2007 | Pruitt et al. | |

FOREIGN PATENT DOCUMENTS

| | | |
|---|---|---|
| EP | 0236014 | 9/1987 |
| EP | 405656 | 1/1991 |
| EP | 1002859 | 5/2000 |
| EP | 971679 | 6/2002 |
| EP | 00845963 | 9/2003 |
| EP | 1083874 | 1/2004 |
| EP | 1089704 | 2/2004 |
| EP | 1098626 | 5/2004 |
| EP | 1437042 | 7/2004 |
| EP | 1612265 | 1/2006 |
| EP | 1337624 | 9/2006 |
| EP | 1702632 | 9/2006 |
| JP | 3273028 | 12/1991 |
| JP | 4-108444 | 4/1992 |
| JP | 4108444 | 4/1992 |
| JP | 7-48769 | 2/1995 |
| JP | 10-136977 | 5/1998 |
| JP | 11180878 | 7/1999 |
| JP | 2001302520 | 10/2001 |
| JP | 2003070466 | 3/2003 |
| JP | 2003189849 | 7/2003 |
| JP | 2003238421 | 8/2003 |
| JP | 3328229 | 11/2003 |
| WO | WO9962491 | 6/1998 |
| WO | WO9844027 | 10/1998 |
| WO | WO9847471 | 10/1998 |
| WO | WO9901034 | 1/1999 |
| WO | WO0003749 | 7/1999 |
| WO | WO9934750 | 7/1999 |
| WO | WO0029553 | 5/2000 |
| WO | WO0045736 | 10/2000 |
| WO | WO0062829 | 10/2000 |
| WO | WO0158413 | 8/2001 |
| WO | WO0166472 | 9/2001 |
| WO | WO0170132 | 9/2001 |
| WO | WO0170289 | 9/2001 |
| WO | WO0170290 | 9/2001 |
| WO | WO0170291 | 9/2001 |
| WO | WO02060396 | 8/2002 |
| WO | WO02070728 | 9/2002 |
| WO | WO03022043 | 3/2003 |
| WO | WO 03/088935 | 10/2003 |
| WO | WO03104443 | 12/2003 |
| WO | WO02015952 | 4/2004 |
| WO | WO2004044188 | 5/2004 |
| WO | WO 2006/020958 | 2/2006 |
| WO | WO 2006/057542 | 6/2006 |
| WO | WO 2007/047707 | 4/2007 |
| WO | WO 2007/062386 | 5/2007 |
| WO | WO 2007/062387 | 5/2007 |
| WO | WO 2007/092929 | 8/2007 |

OTHER PUBLICATIONS

Atala A, & Lanza Rp, eds (2002). Methods of Tissue Engineering, Academic Press, NY.

Atala A. (2004) Tissue engineering and regenerative medicine: concepts for clinical application. Rejuvenation Res 7:15-31.

Bieberich et al., "Differential expresion of the Hox 3.1 gene in adult mouse skin" Ann NY Acad Sci (1991) 642:346-354.
Chase, H.B. et al., "Changes in the skin in relation to the hair growth cycle" The Anatomical Record, The Wistar Institute of Anatomy and Biology, Philadelphia, PA (1953) 116:75-81.
Clark et al., 1988, Mol. Cell. Biol. Of Wound Repair, Plenum Pub., Co. New York.
Coulombe, P.A. And Omary, M.B., "Hard and soft principles defingn the structure, function and regulation of keratin intermediate filaments" Curr Opin Cell Biol (2002) 14:110-122.
Dry, F.W., "The coat of the mouse (Mus musculus)," J. Genetics, Bateson and Punnett eds., (1926) 287-340.
Fieser, L.F. and Fieser, M., "Reagents for Organic Synthesis," John Wiley and Sons, Inc. (1967) 704-706.
Gharzi et al., "Plasticity of hair follicle dermal cells in wound healing and induction," Exp. Dermat. (2003) 12:126-136.
Gilbert, S.F., "Development of the tetrapod limb," Developmental Biology, Sinauer Associates, Inc. (2000) 503-521.
Gurdon, J.B. "The localization of an inductive response" Development (1989) 105:27-33.
Handjiski, B.K. et al., "Alkaline phosphatase activitiy and localizatoin during the murine hair cycle" Br J Dermatol (1994) 131:303-310.
Hansen, L.S. et al., "The influence of the hair cycle on the thickness of mouse skin" Anat Rec (1984) 210:569-573.
Hashimoto et al., "Histological examination of human hair follicles grafted onto severe combined immunodeficient (SCID) mice," Hair Research for the Next Millenium eds., DJJ Van Neste and VA Randall, Elsevier Science BV, Amsterdam (1996) 141-145.
Jahoda, C.A.B. et al., "Hair follicle dermal cells differentiate into adipogenic and osteogenic lineages," Exp. Dermatol. (2003) 12:849-859.
Kanzler, B. et al., "Differential expression of two different homeobox gene families during mouse tegument morphogenesis," Int. J. Dev. Biol. (1994) 38:633-640.
Katayama, S. et al., "Synthesis of Alternating Polyamide Esters by Melt and Solution Polycondensations of N,N'-Di(6-hydroxycaproyl) dimines and N-6-Hydroxycaproyl Aminoalcohol with Terephthalic and Adipic Dimethyl Esters and Dichlorides" J. of Applied Polymer Science (1976) 20:975-994.
Kaufman, C.K. et al., "GATA-3: an unexpected regulator of cell lineage determination in skin," Gene Dev (2003) 17:2108-2122.
Ma, L. et al., "Cyclic alopecia in Msx2 mutants: defects in hair cycling and hair shaft differentiation" Development (2003) 130:379-389.
Messenger, "Hair Follicle Tissue Culture" Br. J. Dermatol. (1985) 113:639-640.
Mills, A.A. et al., "p63 is a p53 homologue required for limb and epidermal morphogenesis," Nature (1999) 398:708-713.
Moscona, A., "Rotation-mediated histogenetic aggregation of dissociated cells. A quantifiable approach to cell interactions in vitro," Exp. Cell Research (1961) 22:455-475.
Paus, R. et al., "Telogen skin contains an inhibitor of hair growth," Brit J Dermatol (1990) 122:777-784.
Philpott, M. et al., "In vitro maintenance of isolated hair follicles: current status and future development," Ex. Dermatol. (1999) 8(4):317-319 Abstract.
Pispa, J. and Thesleff, I., "Mechanisms of ectodermal organogenesis," Dev Biol (2003) 262:195-205.
Powell, B.C. et al., "The Notch Signalling pathway in hair growth" Mech Dev (1998) 78:189-192.
Prouty, S.M. et al., "Fibroblast-dependent induction of a murine skin lesion similar to human nevus sebaceus of jadassohn," Lab. Invest (1997) 6(2):179-189.
Prouty, S.M. et al., "Fibroblast-dependent induction of a murine skin lesion with similarity to human common blue nevus" Am J Pathol. (1996) 148(6):1871-1885.
Sambrook et al., 1989, Molecular Cloning: A Laboratory Manual, Cold Spring Harbor Laboratory, New York.
Scholer, H.R. et al., "A family of octmer-specific proteins present during mouse embryogenesis: evidence for germline-specific expression of an Oct factor," Embo J (1989) 8(9):2543-2550.

Schwarz, Ma et al., "Epithelial-mesenchymal interactions are linked to neovacsularization" Amer J Respir Cell Mol Biol (2004) 30:784-792.
Stenn et al., "Re-epithelialization," Chapter 14 in: the Molecular and Cellular Biology of Wound Repair, Eds, Raf Clark, Plenum Press (1988) 321-335.
Stenn, K. et al., "Growth of the Hair Follicle: A Cycling and Regenerating Biological System," The Molecular Basis of Epithelial Appendage Morphogenesis, ed. C-M Chuong, Landes Publ. Austin TX (1998) 111-130.
Takeda, A. et al., "Histodifferentiation of hair follicles in grafting of cell aggregates obtained by rotation culture of embryonic rat skin" Scand J. Plas Reconstr Hand Surg (1998) 32:359-364.
Takeda, A. et al., "Reconstitution of hair follicles by rotation culture," Hair Research for the Next Millennium, eds. Van Neste and Randall, Elsevier Science BV (1996) 191-193.
Tsonis, P.A. Limb Regeneration, Cambridge University Press, Cambridge (1996) 241.
Widelitz, R.B. And Chuong, C-M., "Early events in skin appendage formation: Induction of epithelial placodes and condensation of dermal mesenchyme," J Invest Dermatol Sympos Proc (1999) 4(3):302-306.
Williams, D. et al., "Isolation and culture of follicular papillae from murine vibrissae: an introductory approach," Br. J. Dermatol. (1994) 130:290-297.
Xing, L and Kobayashi, K., "Ability of Transplanted Cultured Epithelium to Respond to Dermal Papillae," Tissue Engineering (2001) 7:535-544.
Atlas of Anatomy Barron's Educational Series, Inc., 1997, p. 72.
Arase, Seigi, et al., Tokushima *J. exp. Med*. 36: 87-95 (1989).
Barrows TH, Cochran SA, Griffin EI and Solomon AR, "Tissue Engineered Human Hair: Preliminary Clinical Results" *TE2002: International Workshop on Tissue Engineering*, St. Gallen, Switzerland (Feb. 2002).
Bioglass, http://www.usbiomat.com/bioglass.html Dec. 28, 2000.
Chang et al (2004) "Sculpting skin appendages out of epidermal layers via temporally and spatially regulated apoptotic events" *J Invest Dermatol* 122:1348-1355.
Chiang et al., 1999, "Essential Role for Sonic hedgehog during Hair Follicle Morphogenesis," *Dev. Biol*. 205:1-9.
Cohen J, "The transplantation of individual rat and guinea-pig whisker papillae," *J Embryol Exp Morphol*. Mar 1961;9:117-27.
Cotsarelis G, Sun TT, Lavker RM. (1990) Label-retaining cells reside in the bulge area of pilosebaceous unit. Implications for follicular stem cells, hair cycle and skin carcinogenesis *Cell* 61:1329-1337.
Csiro et al., *Arch Dermatol Res*. 183(5):321-327 abstract.
Deleens, G., et al., *SPIE 39th Ann. Tech. Cont*., Boston, MA 5/4-7/81.
Dlugosz, (1999), "The Hedgehog and the hair follicle: a growing relationship", *The Journal of Clinical Investigation*, vol. 104, 851-853.
Domashenko, et al., (2000), "Efficient delivery of transgenes to human hair follicle progenitor cells using topical lipoplex", *Nature Biotechnology*, vol. 18, 420-423.
Du Cros et al. (1995) Association of versican with dermal matricies and its potential role in hair follicle development and cycling: *J Invest Dermatol* 105:426-31.
Dyce et al., (2004) "Stem cells with multilineage potential derived from porcine skin" *Bioche Biophys Res Commun*, 316:651-658.
Ebling FJ, "The biology of hair," *Dermatol Clin* 1987 Jul.;5(3):467-81.
Elsdale T, and Bard J, (1972) "Cellular Interactions in Mass Cultures of Human Diploid Fibroblasts" *Nature* 236:152-155.
Evans, G.R., Brandt, K, Widmer, M.S., Lu, L., Meszlenyi, R.K, Gupta, P.K., Mikos, A.G., Hodges, J., Williams, J., Gurlek, A., Nabawi, A., Lohman, R., and Patrick, C.W. Jr., "In vivo evaluation of poly(L-lactic acid) porous conduits for peripheral nerve regeneration" *Biomaterials*20 (1999) 1109-1115.
Favier B, et al. "Localisation of members of the notch system and the differentiation of vibrissa hair follicles: receptors, ligands, and fringe modulators" *Dev Dyn* Jul. 2000;218(3):426-37.
Ferraris et al., 1997, "Adult epidermal keratinocytes are endowed with pilosebaceous forming abilities" Int *J. Dev. Biol*., 41:491-498.

Foitzik, et al., (2000) "Control of murine hair follicle regression (catagen) by TGF-B1 in vitro", Catagen Induction by TGF-B1, The Faseb Journal, vol. 14, 752-760.

Fujie et al. (2001) "The chemotactic effect of a dermal papilla cell-derived factor on outer root sheath cells," J. Dermatol. Sci. 25(3):206-12.

Gambardella et al., (2000) "Pattern of Expression of the Transcription Factor Krox-20 in mouse hair follicle", Mech. Of Dev. 96:215-218.

Hage JJ and Freerk GB, (1991) "Surgical Depilation for the Treatment of Pseudofolliculitis or Local Hirsutism of the Face: Experience in the First 40 Patients" Surgical Depilation for Pseudofolliculits, 88(3) 446-451.

Hardy M, (1949) "The development of mouse hair in vitro wit some observations on pigmentation" J. Anat, 83:364-384.

Hardy, M., (1992) "The Secret Life of the Hair Follicle," Trends in Genetics 8:55-61.

Haynesworth, et al., (1993) "Diminution of the Number of Mesenchymal Stem Cells as a Cause for Skeletal Aging" Chapter 7, 79-87.(Eds. J.A. Buckwater & V.M. Goldberg).

Horne et al., (1992) Development 116(3), abstract.

Horne, Kenneth A, et al. "Whisker growth induced by implantation of cultured vibrissa dermal papilla cells in the adult rat" J Embryol Exp Morphol. Sep. 1986;97:111-24.

Hu M, Sabelmann EE, Lai S, Timek EK, Zhang F, Hentz, VR and Lineaweaver, CW, Journal of Biomedical Materials Research, vol. 47, pp. 79-84 (1999).

Inaba (1992) "Chapter 16. The Question of Hair Regeneration. In: Human Body Odor, Etiology Treatment and Related Factors" Springer-Verlag, Tokyo (printed in Hong Kong) 235-260.

Inamatsu et al., "Establishment of rat dermal papilla cell lines that sustain the potency to induce hair follicles from afollicular skin" J Invest Dermatol. Nov. 1998;111(5):767-75.

Jahoda and Oliver, (1981), Br. J. Dermatol., 105:623-627.

Jahoda and Reynolds (2001) "Hair follicle dermal sheath cells: unsung participants in wound healing" Lancet 358:1445-1448.

Jahoda Cab, et al., (1996) "Human Hair follicle regeneration following amputation and grafting into the nude mouse" J Invest Dermatol, 107(6):804-807.

Jahoda Cab, et al., "Induction of hair growth by implantation of cultured dermal papilla cells" Nature. Oct. 11-17, 1984;311(5986):560-2.

Jahoda Cab, et al. (1993) "Induction of Hair Growth in Ear Wounds by Cultured Dermal Papilla Cells" J Invest Dermatol 101(4):584-590.

Jahoda, Cab, et al. Journal of Investigative Dermatology 101(1), Supplement Jul. 1993, 33S-38S.

Jahoda Cab, "Induction of follicle formation and hair growth by vibrissa dermal papillae implanted into rat ear wounds: vibrissa-type fibres are specified," Development (1992) 115(4):1103-1109.

Jahoda et al. "Dermal-Epidermal Interactions, Adult Follicle-Derived Cell Populations and Hair Growth" Dermatologic Clinics W. B. Saunders Co. London G.B., Oct. 1996, 14(4):573-583; XP002913549.

Jahoda, et al., (2001) "Trans-species hair growth induction by human hair follicle dermal papillae," Exp. Dermatol. 10:229-237.

Kamimura, et al. Journal of Investigative Dermatology 109(4), Oct. 1997, 534-540.

Kemp CB, et al., (1973) "Effect of Transplantation Site on the Results of Pancreatic Islet Isografts in Diabetic Rats" Diabetologia 9:486-491.

Kishimoto et al., "Selective activation of the versican promoter by epithelial- mesenchymal interactions during hair follicle development" Proc Natl Acad Sci U S A. Jun. 22, 1999;96(13):7336-41.

Kishimoto, et al., "Wnt signaling maintains the hair-inducing activity of the dermal papilla" Genes Dev. May 15, 2000:14(10):1181-5.

Lako et al., (2002) Hair follicle dermal cells repopulate the mouse haematopoietic system: J. Cell Sci 115:3967-3974.

Lanford PJ, et al. Notch signalling pathway mediates hair cell development in mammalian cochlea? Nat. Genet Mar. 1999;21(3):289-92.

Lavker, RM, et al. Journal of Investigative Dermatology 101(1), Supplement, Jul. 1993, 16S-26S.

Lewis AK, et al. "Distinct expression patterns of notch family receptors and ligands during development of the mammalian inner ear" Mech Dev Nov. 1998:78(1):159-163.

Lichti et al., "In vivo regulation of murine hair growth: insights from grafting defined cell populations onto nude mice" J Invest Dermatol. Jul 1993;101(1 Suppl):124S-129S.

Lichti, et al. Journal of Investigative Dermatology 104(5), Supplement, May 1995, 43S-44S.

Lin et al., 2000 Development, 127:2421-2432.

Ma, Peter X., Ruiyun Zhang, "Synthetic nano-scale fibrous extracellular matrix" J. Biomed. Materials Res. 46(1):60-72 (Jul. 1999).

Malkinson F and Keane JT, (1978) "Hair Matrix Cell Kinetics; A Selective Review" Int'l J Dermatol, 17(7):536-551.

Matsuzaki et al., Differentiation, 60(5):287-297 abstract.

McElwee et al., "Cultured Peribulbar Dermal Sheath Cells Can Induce Hair Follicle Development and Contribute to the Dermal Sheath and Dermal Papilla" 2003 J. Invest Dermatol 121:1267-1275.

Messenger AG, "The control of hair growth: an overview" J Invest Dermatol Jul. 1993;101(1 Suppl):4S-9S.

Messenger, (1984) British Journal of Dermatology 110, 685-689.

Michalopoulos G. and Pitot He, (1975) "Primary Culture of Parenchymal Liver Cells on Collagen Membranes" Experimental Cell Research 94:70-78.

Morris RJ., Liu Y, Marles L, Yang Z, Trempus C, Li S, Lin JS, Sawicki JA, & Cotsarelis G. (2004) Capturing and profiling adult hair follicle stem cells. Nature Biotechnology 22:411-417.

Nam, Y.S. and T.G. Park, "Porous biodegradeable polymerick scaffolds prepared by thermally induced phase separation" The Journal of Biomedical Materials Research, Oct. 1999, 47(1): 8-17.

Nichols et al. (1998) "Formation of pluripotent stem cells in the mammalian embryo depends on the POU transcription factor" Oct. 4, Cell 95:379-391.

Nixon et al., 1996, "Transforming Growth factor-alpha Immunoreactivity During Induced Hair Follicle Growth Cycles in Sheep and Ferrets" J. Histochem. Cytochem, 44:377-387.

Oliver RF, (1971) "The dermal papilla and the development of hair growth" J Soc Cosmet Chem 22:741-755.

Oliver RF, "The experimental induction of whisker growth in the hooded rat by implantation of dermal papillae" J Embryol Exp Morphol. Aug. 1967;18(1):43-51.

Oliver RF, "Histological studies of whisker regeneration in the hooded rat." J Embryol Exp Morphol. Oct. 1966;16(2):231-44.

Oliver RF, "The induction of hair follicle formation in the adult hooded rat by vibrissa dermal papillae" J Embryol Exp Morphol. Feb. 1970;23(1):219-36.

Oliver RF (1980) "Local interactions in mammalian hair growth" Mammalian Hair Growth, 199-210.

Oliver RF, "Whisker growth after removal of the dermal papilla and lengths of follicle in the hooded rat" J Embryol Exp Morphol. Jun. 1966;15(3):331-47.

Oliver RF and Jahoda Cab, (1989) "The Dermal Papilla and Maintenance of Hair Growth" Dermal Papilla and Hair Growth Chapter 4, 51-67. Cambridge: Cambridge University Press.

Oshima et al., (2001) "Morphogenesis and renewal of hair follicles from adult multipotent stem cells" Cell, 104:233-245.

Patrick, C.W., A.G. Mikos and L.V. McIntire, eds., Prospects of Tissue Engineering, Frontiers in Tissue Engineering, Elsiver Science, Inc., New York, (1998).

Paus et al. (1999) "A comprehensive guide for the recognition and classification of distinct stages of hair follicle morphogenesis" J Invest Dermatol 113:523-532.

Philpott et al., 1994, "Effects of Insulin and Insulin-Like Growth Factors on Cultured Human Hair Folicles: IGF-1 at Physiologic Concentrations Is an Important Regulator of Hair Follicle Growth In Vitro" J. Invest. Derm., 120:857-861.

Raposio, Edoardo, et al., Plastic and Reconstructive Surgery, 221-226 (1998).

Reginelli et al. (1995) "Digit tip regeneration correlates with regions of Msx1 (Hox 7) expression in fetal and newborn mice" Development 121:1065-1076.

Remmler D, Thomas JR, Mazoujian G, Pentland A, Schechtman K, Favors S, and Bauer E, Arch Otolaryngol Head Neck Surg Jul. 1989; 115:837-44.

Reynolds & Jahoda (1992) "Cultured dermal papilla cells induce follicle formation and hair growth by transdifferentiation of an adult epidermis" *Development* 115:587-593.

Reynolds & Jahoda, (1993) "Hair fibre progenitor: developmental status and interactive potential" *Dev Biol*, 4:241-250.

Reynolds & Jahoda, "Hair follicle reconstructive in vitro" *J. Dermatol Sci* Jul. 1994;7 Suppl:S84-97.

Reynolds & Jahoda, (1991a) "Inductive Properties of Hair Follicle Cells" Annals New York Academy of Sciences, 624:226-242.

Reynolds AJ, et al. (1992) "Human Hair Follical Germinative Epidermal Cell Culture" *J Invest Dermatol*, 101(4): 634-638.

Reynolds, AJ, et al., *Nature* 402: 33-34, (Nov. 4, 1999).

Rogers et al. "Cultivation of murine hair follicles as organoids in a collagen matrix" *J Invest Dermatol*. Oct. 1987;89(4):369-79.

Sato, et al., (1999), "Induction of the hair growth phase in postnatal mice by localized transient expression of sonic hedgehog", *J. Clin. Invest.* 104:855-864.

Scott DM, et al. (1995) "Identification of a mouse male-specific transplantation antigen, H-Y" *Nature* 376:695-698.

Stenn and Paus, "Controls of Hair Follicle Cycling" *Physiological Reviews*, vol. 81, No. 1, Jan. 2001, pp. 449-494.

Stenn, et al., (1996) *Dermatol Clinics* 14:543-558.

Stenn KS, "Induction of hair follicle growth" *J. Invest Dermatol* May 1991;96(5):80S.

Sundberg et al. (2000) "Asebia-2J(Scd1(ab2J)): a new allele and a model for scarring alopecia" *Amer J Path* 156:2067-2075.

Taylor et al., (2000) "Involvement of follicular stem cells in forming not only the follicle but also the epidermis" *Cell* 102:451-461.

Tomihata K and Ikada Y, "Crosslinking of hyaluronic acid with water-soluble carbodiimide" *J. Biomed. Mater. Res.* 37, 243-251 (1997).

Trempus et al. (2003) "Enrichment for living murine keratinocytes from the hair follicle bulge with the cell surface marker CD34" *J Invest Dermatol* 120:501-11.

Watson Saj, et al., (1994) "Sheep vibrissa dermal papillae induce hair follicle formation in heterotypic skin equivalents" *Br J Dermatol*, 131:827-835.

Weinberg, et al. Reconstruction of hair follicle development in vivo: determination of follicle formation, hair growth, and hair quality by dermal cells: *Journal of Investigative Dermatology* 100(3), Mar. 1993, 229-236.

Widelitz et al., 1997, "Molecular Histology in Skin Appendage Morphogenesis" *Microsc., Res. Tech.*, 38:452-465.

Wilson C. et al., "Cells within the bulge region of mouse hair follicle transiently proliferate during early anagen: heterogeneity and functional differences of various hair cycles" *Differentiation* Jan. 1994;55(2):127-36.

Yagita (1996) "CD95 ligand graft rejection" *Nature* 379:682-683.

Yang et at (1999) p63 is essential for regenerative proliferation in limb, craniofacial and epithelial development: *Nature* 398:714-718.

Yang, et al., (1993), "Upper-Human Hair Follicle Contains a Subpopulation of Keratinocytes with Superior In Vitro Proliferative Potential", in vitro Growth of Follicular Keratinocytes, *The Journal of Investigative Dermatology*, vol. 101, No. 5, 652-659.

Yuspa Sh, et al., Journal of Investigative *Dermatology* 101(1), Supplement, Jul. 1993, 27S-32S.

Stenn, K.S. et al., "Bioengineering the hair follicle: fringe benefits of stem cell technology," Curr. Opin. Biotech. (2005) 16(5):493-497.

Worst, P.K.M. et al., "Reformation of organized epidermal structure by transplantation of suspensions and cultures of epidermal and dermal cells," Cell Tiss. Res. (1982) 225(1):65-77.

Zheng, Y. et al., "Organogenesis from dissociated cells: generation of mature cycling hair follicles from skin-derived cells," J. Invest. Dermatol. (2005) 124:867-876.

U.S. Appl. No. 11/811,744, filed Jun. 12, 2007, Zheng et al.

Auger et al., "A truly new approach for tissue engineering: the LOEX self-assembly technique" Ernst Schering Res. Found. Workshop (2002) 35:73-88.

Barrows, "Project One: Update Report, Jul. 3-30, 2004" (2004) 2-3.

Claudinot et al., "Long-term renewal of hair follicles from clonogenic multipotent stem cells," PNAS (2005) 102:14677-14682.

Cotsarelis, G. et al., "Towards a molecular understanding of hair loss and its treatment," Trends Mol. Med. (2001) 7:293-301.

Gho et al., "Hair transplantation of plucked hair biopsies," Dermatol. Surg. (2001) 27(10):913.

Gho et al. To Multiply or Not to Multiply, That is the Question..., Dr. Coen Gho presentation at the International Society of Hair Restoration Surgeons 2003 New York City Conference, Oct. 19, 2003 (Abstract).

Horch, R.E. et al., "Tissue engineering of cultured skin substitutes," J. Cell Mol. Med. (2005) 9(3):592-608.

Ihara, S. et al., "Formation of hair follicles from a single-cell suspension of embryonic rat skin by a two-step procedure in vitro," Cell Tissue Res. (1991) 266:65-73.

Krugluger, W. et al., "Reorganization of hair follicles in human skin organ culture induced by cultured human follicle-derived cells," Exp. Dermatol. (2005) 14(8):580-585.

Layer, P.G. et al., "Of layers and spheres: the reaggregate approach in tissue engineering," Trends Neurosci. (2002) 25:131-134.

Lee, K.H., "Tissue-engineered human living skin substitutes: development and clinical application," Yonsei Med. J. (2000) 41(6):774-779.

Luo et al., U.S. Statutory Invention Registration H1610, Published Nov. 5, 1996, Methods for Culturing Hair Follicle Epithelial Matrix Cells.

Luo Y., et al. "Modification of Natural Polymers: Hyaluronic Acid," Methods of Tissue Engineering, Chapter 45, A. Atala and RP Lanza. eds., Academic Press (2002) 539-553.

Magerl, M. et al., "Simple and rapid method to isolate and culture follicular papillae from human hair follicles," Exp. Dermatol. (2002) 11:381-385.

Matsuzaki et al., "Localization and migration of follicular melanocyte precursors in mouse vibrissae during hair cycle," Zoological Science (2002) 19(12):1450.

Mayorov, V.I. et al., "B2 elements present in the human genome," Mamm. Genome (2000) 11:177-179.

Michel et al., "Characterization of a new tissue-engineered human skin equivalent with hair," in Vitro Cell Dev Biol. Anim. (1999) 35(6):318-326.

Misago, N. et al., "Proliferation and differentiation of organoid hair follicle cells co-cultured with fat cells in collagen gel matrix culture," Br. J. Dermatol. (1998) 139(1):40-48.

Miyashita et al., "Characterization of hair follicles induced in implanted, cultured rat keratinocyte sheets," Exp. Dermatol. (2004) 13(8):491-498.

Oliver, R.F., "Ectopic regeneration of whiskers in the hooded rat from implanted lengths of vibrissa follicle wall," J. Embryol. Exp. Morphol. (1967) 17:27-34.

Osada et al., "Characterization of vibrissa germinative cells: transition of cell types," Exp. Dermatol. (2001) 10:430-437.

Pouliot et al., "Reconstructed human skin produced in vitro and grafted on athymic mice," Transplantation (2002) 73(11):1751-1757.

Price, V.H., "Treatment of Hair Loss," N Eng J Med (1999) 341:964-973.

Ratner, B.D. et al., "Biomaterials: where we have been and where we are going," Annu. Rev. Biomed. Eng. (2004) 6:41-75.

Robinson, M. et al., "Hair cycle stage of the mouse vibrissa follicle determines subsequent fiber growth and follicle behavior in vitro," J. Invest. Dermatol. (1997) 108:495-500.

Saywell, D.P. et al., "Cell proliferation during fibre growth initiation in ferret hair follicles," Proceedings of the New Zealand Society of Animal Production (1992) 52:299-302.

Stenn et al., "Bioengineering the hair follicle: fringe benefits of stem cell technology," Curr. Opin. In Biotech. (2005) 16:1-5.

Thornton, M.J. et al., "Ability to culture dermal papilla cells from red deer (Cervus elaphus) hair follicle differing hormonal responses in vivo offers a new model for studying the control follicle biology," J. Experimental Zoology (1996) 275(6):452-458.

Yang et al., "Cell sheet engineering: recreating tissue without biodegradable scaffolds," Biomaterials (2005) 26(33):6415-6422.

\* cited by examiner

TISSUE ENGINEERED BIOMIMETIC HAIR FOLLICLE GRAFT

CROSS-REFERENCE TO RELATED APPLICATIONS

Not Applicable

STATEMENT REGARDING FEDERALLY SPONSORED RESEARCH OR DEVELOPMENT

Not Applicable

INTRODUCTION

Male pattern baldness is a common condition that is often treated by hair transplant surgery. In this procedure hair follicles from areas of the scalp that are not within the baldness pattern are excised and re-implanted within the baldness pattern to create the illusion of a fuller head of hair. No new hair is created by this procedure. Its success is limited by the number of follicles that can be harvested and re-implanted into the baldness pattern. Moreover, since not all explanted follicles are successfully transplanted, this technique, while the best available, has significant shortcomings.

It is well known that specific types of cells found in substructures within the hair follicle have the capacity to induce the formation of complete, normally functioning hair follicles. Such cells are known as follicular stem cells or follicle progenitor cells. In view of the large market for an effective hair restoration treatment, many attempts have been made to exploit the follicle-inducing capacity of these cells for the purpose of hair multiplication. Although apparently scientifically feasible, all schemes disclosed in the prior art have proven to fall short of the goal of providing a clinically and cosmetically acceptable new treatment for baldness. For example, cultured dermal papilla cells from a rat whisker were implanted just under the skin on a rat's ear, resulting in the growth of whiskers from the site of implantation. Cf., R. F. Oliver and C. A. B. Jahoda in U.S. Pat. No. 4,919,664, "Stimulation of hair growth", Apr. 24, 1990, the teachings of which are incorporated by reference herein. In an unpublished clinical study of 5 human volunteers by Dr. Andrew Messenger, hair follicle dermal papilla cells dissected from scalp biopsies of the volunteers were cultured. The cells were multiplied and covered the surface of the culture flask, were removed by scraping them off the surface of the flask, and implanted into shallow incisions in the skin on the underside of the forearm in each subject from whom the cells were obtained. No new hair growth was observed at the sites of cell implantation. All sites were biopsied after 6 months and the histological findings were normal with no evidence of scalp hair follicle formation.

More recently, T. H. Barrows described in International Publication WO 02/15952, "Scaffolds for Tissue Engineered Hair", Feb. 28, 2002, the teachings of which are incorporated herein, a method of implanting the same type of cultured cells on a porous "scaffold" made from a bioabsorbable material. A subsequent clinical study in this case produced the first documented example of the induction of new hair follicles and hair growth in the skin of a human subject from the implantation of cultured cells (see T. H. Barrows, S. A. Cochran, E. I. Griffin, and A. R. Solomon, "Tissue Engineered Human Hair: Preliminary Clinical Results", TE2002: *International Workshop on Tissue Engineering*, St. Gallen, Switzerland, 24-27 Feb., 2002, the teachings of which are incorporated by reference herein). Cells injected without the presence of a solid scaffold structure failed to show any evidence of follicle neogenesis. However, only one out of 16 implantations of cells in combination with scaffolds actually resulted in the growth of cosmetically useful hair shafts. Although equivocal evidence of follicle neogenesis in a number of the cell-plus-scaffold implant sites was noted histologically, there was also a persistent inflammatory response to residues of partially degraded scaffold debris. This type of foreign body response has been postulated to create a detrimental environment for hair follicle formation (see K. S. Stenn, "Compositions and methods for inducing new hair follicle formation and hair growth in a desired orientation", U.S. patent application Ser. No. 10/123,984, Apr. 17, 2002, the teachings of which are incorporated herein).

Thus there remains an unmet need for a reliable and reproducible method for culturing hair follicle progenitor cells and implanting the cultured cells into skin such that new, cosmetically viable hair follicles are created.

SUMMARY OF THE INVENTION

Briefly, in one aspect, the present invention is an improved scaffold which is constructed to mimic the architecture of the native hair follicle and which is designed for percutaneous implantation. Portions of the implant serve as supporting structures for the seeding of specific types of cells and other portions in contact with or protruding through the epidermis serve as a site for epidermal down-growth. This down-growth is beneficial in creating an infundibulum in communication with the implanted cells, which in turn is helpful in controlling the angle of egress of the newly forming hair shaft.

In another aspect, the present invention is the use of specific compositions and methods of manufacture to produce scaffolds that combine biocompatibility with the desired rates of bioabsorption. The performance characteristics of these types of scaffolds are critically important in the construction of a successful follicle-inducing implant, which facilitates or enhances the follicle neogenesis process.

In yet another aspect, the present invention is a specific combination of cultured cells that provide reliable and reproducible initiation of follicle neogenesis. The implantation of cultured dermal papilla (also known as follicular papilla) cells alone gives unpredictable, non-reproducible results. It has been found that keratinocytes, suitably keratinocytes obtained from neonatal skin (e.g. infant foreskin tissue), also must be implanted in combination with the dermal papilla cells. Other types of cells optionally also can be combined with the dermal papilla/keratinocyte combination to improve the success rate of follicle neogenesis. Optional additional cells may be selected from stem cell populations that are known to exist in human embryo, fetal or infant scalp skin, infant foreskin, umbilical cord blood, adult bone marrow, muscle, adipose tissue, and skin.

A further aspect of the present invention is the surprising discovery of chondroitin-6-sulfate as a substance that provides a beneficial effect upon, or enhancement of, the follicle neogenesis process.

In another aspect, the present invention is a process for manufacturing a biomimetic hair follicle graft and a method for seeding it with cells and implanting it into skin where the growth of a new hair shaft is desired.

A further aspect of the present invention is a method for hair multiplication in which cells from harvested follicles, are multiplied in culture, and aliquoted into a multitude of bioabsorbable scaffolds in combination with cultured keratinocytes or other allogeneic cells. Implantation of the resultant cell-seeded biomimetic grafts provides a higher degree of hair restoration than possible by methods of the prior art. Thus the method of the present invention reduces, inhibits or cures loss of hair specifically including, but not limited to, male or female pattern baldness and other hair loss conditions.

BRIEF DESCRIPTION OF THE DRAWINGS

FIG. 6 also shows a filament (11) made of PLGA containing no HAX. Both filaments were placed on a drop of water (12) colored red with food color dye. The PLGA only fiber (11) floated on the top of the water and did not wick any water into the lumen of the fiber, whereas the HAX-containing PLGA fiber (10) rapidly wicked the water into the lumen, giving the fiber a red color.

DEFINITIONS

Figure 1:
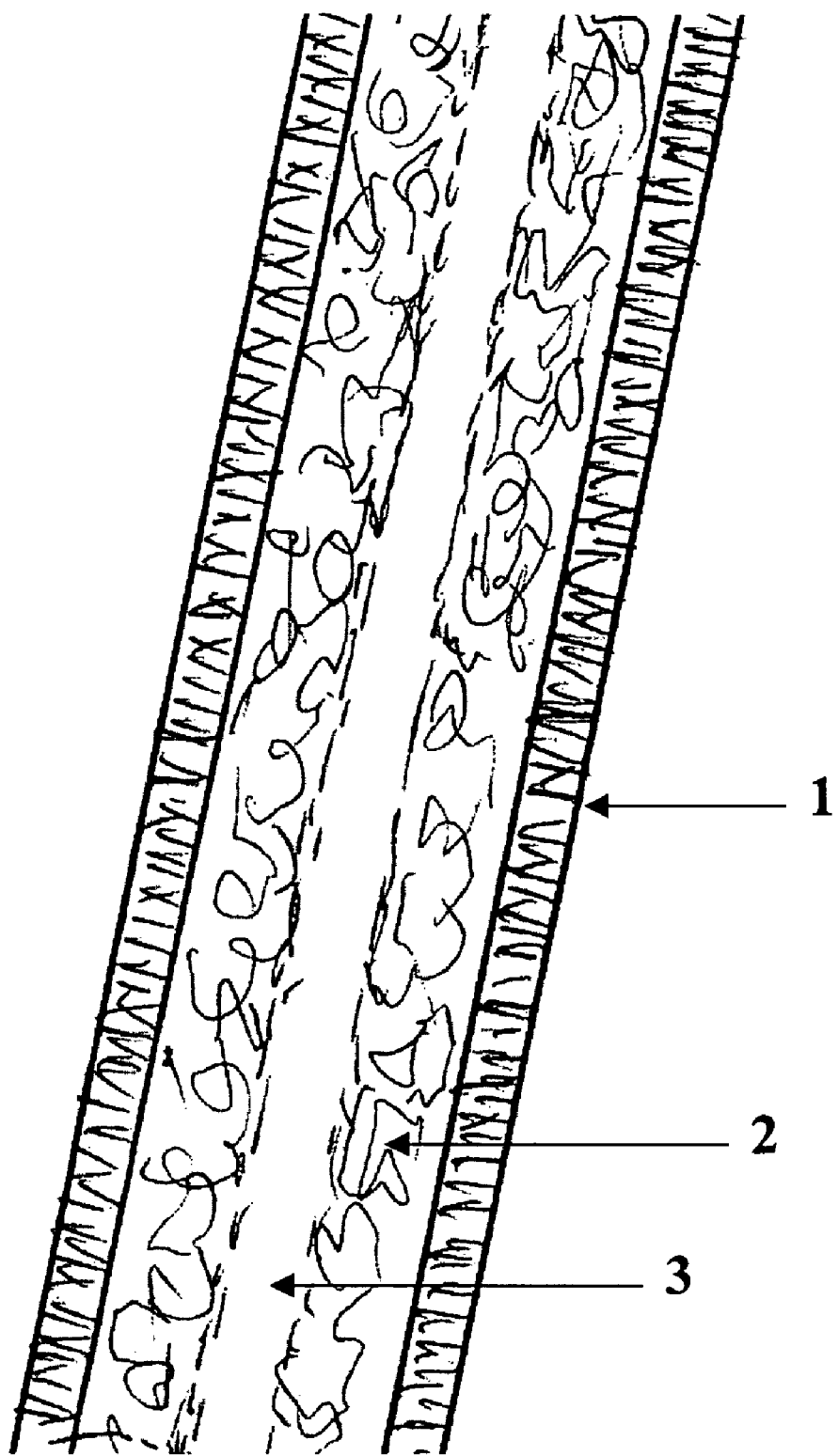
FIG. 1 is a cross-sectional schematic representation of a hollow filament of the present invention showing a solid outer filament (1) of bioabsorbable polymer, a porous inner filament (2) of the same or different bioabsorbable polymer, and a central lumen (3).
Figure 2:
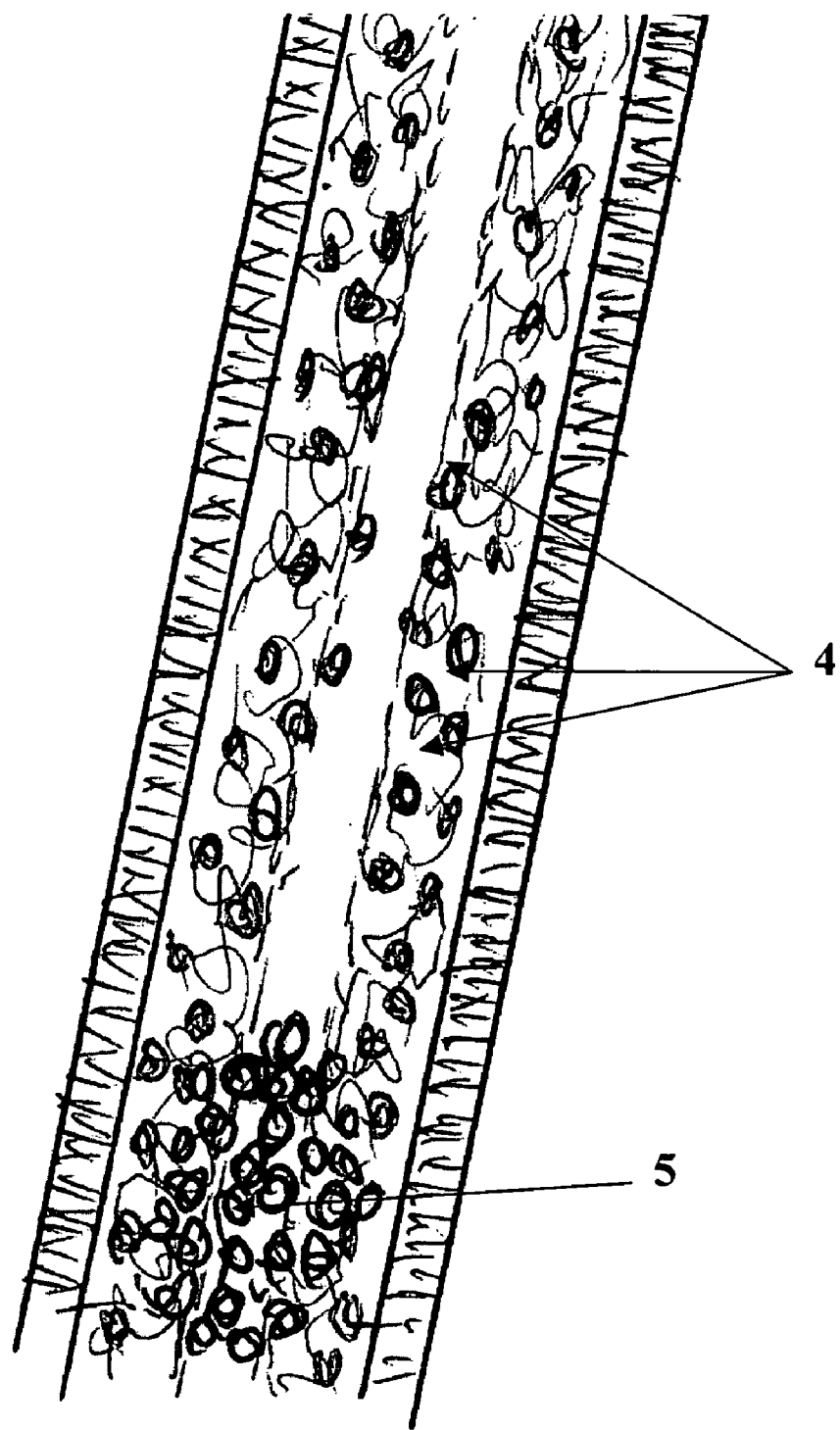
FIG. 2 is a cross-sectional schematic representation of the hollow filament of FIG. 1 showing cells (4) (e.g. keratinocytes) that have been seeded into the porous inner filament by wicking a suspension of cells into the lumen of the filament and a clump of cells (5) (e.g. cultured dermal papilla cells or a hair follicle fragment) that has been seeded into the lumen of the filament by mechanically forcing it into an open end of the filament.
Figure 3:
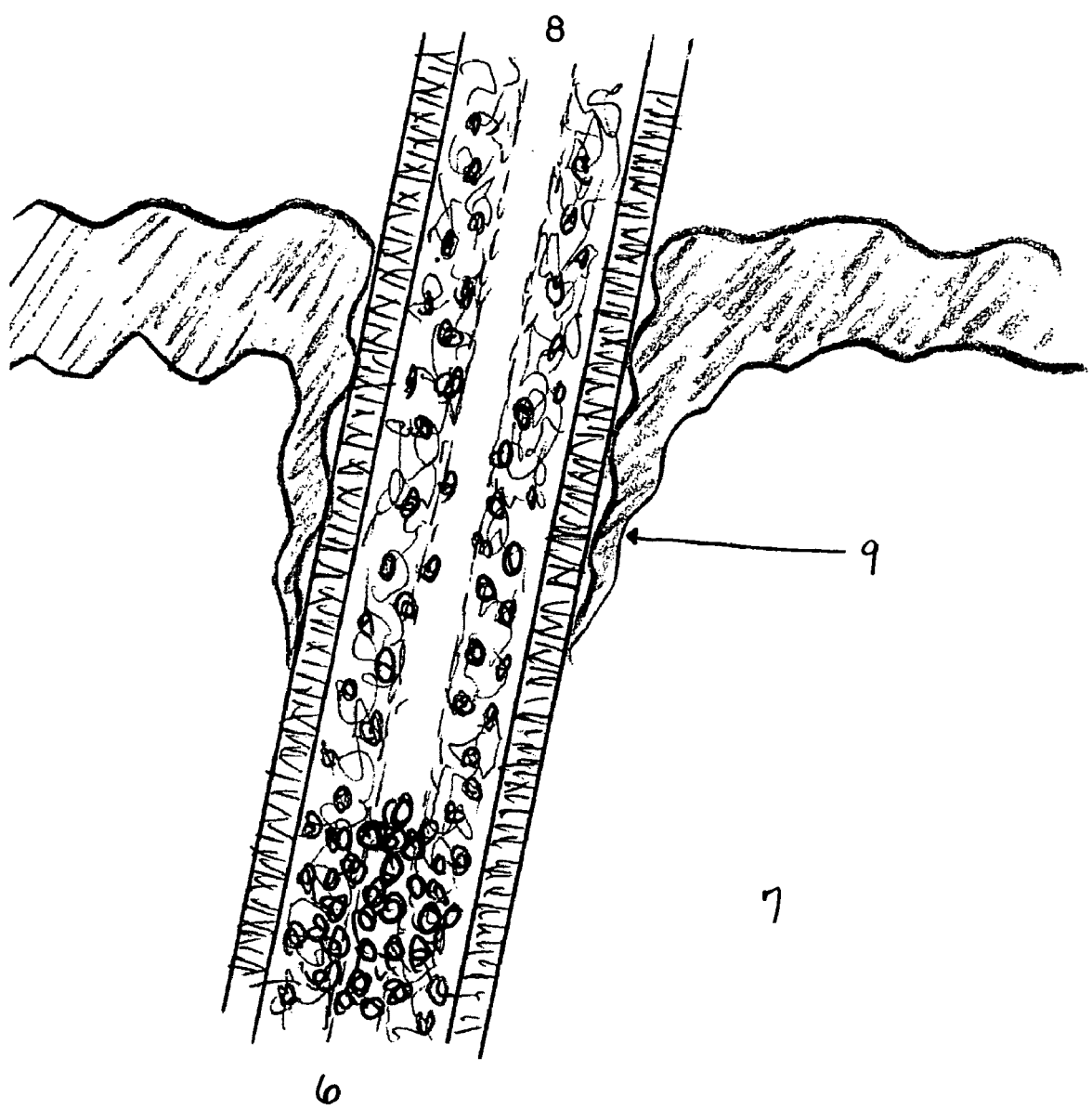
FIG. 3 is a cross-sectional schematic representation of the filament of FIG. 2 shortly after implantation in the skin such that the proximal end (6) is in the dermis (7) and the distal end (8) is surrounded by down-grown epidermis (9).

As used herein, the terms listed below shall have the following meanings:

"Tissue engineering" is defined as the art of creating combinations of cells, biocompatible scaffolds, usually bioabsorbable scaffolds, that have utility in replacing, repairing, or augmenting tissues and organs of the human body.

"Follicle neogenesis" is defined as the phenomenon of new hair follicle formation in a region of the skin where none previously existed or in addition to and among pre-existing follicles.

"Bioabsorbable" is defined as the property of a material that allows it to be broken down in the body into non-toxic by-products that are excreted from the body or metabolized therein.

"Scaffold" is defined as a non-cytotoxic structure that is capable of containing living cells and holding them in a specified configuration.

"Filament" is defined as a cylindrical structure that has a length that is greater than its diameter.

"Fiber" is defined as a filament that possesses physical integrity.

"PLGA" is defined as a copolymer of lactide and glycolide.

"VEGF" is defined as vascular endothelial growth factor.

"EDC" is defined as N-(3-dimethylaminopropyl)-N'-ethylcarbodiimide hydrochloride.

"TFE" is defined as 2,2,2-trifluoroethanol.

"HAX" is defined as crosslinked hyaluronic acid.

"Mandrel" is defined as a cylindrical, tapered, or conical object used to hold the shape of materials applied to its outer surfaces and is removed in a process that yields a hollow filament from said applied materials.

DETAILED DESCRIPTION OF THE INVENTION

In an embodiment of the present invention, the scaffold component of the biomimetic hair follicle graft is a hollow filament comprised of one or more bioabsorbable polymers which define an interior lumen generally extending from one end of the scaffold to the other. The interior walls of the hollow filament or the exterior walls can be either smooth or porous depending upon the desired use. For example, a hollow filament with a relatively smooth surface can be used to retain one type of cell (e.g. human foreskin keratinocytes) on the lumenal surface and another type of cell (e.g. cultured adult human hair follicle papilla cells, suitably in the form of an aggregated clump of cells), positioned within the lumen and in contact with the surrounding surface-attached cells. A hollow filament with a highly porous, hydrophilic interior can be used to wick a suspension of cells of one or more type into the filament, which by itself may be relatively hydrophobic and therefore not capable of wicking aqueous fluid.

The porous, hydrophilic interior may have a faster rate of bioabsorption or liquefaction than the exterior of the hollow filament to facilitate reorganization of the seeded cells within the lumen of the filament while continuing to be contained by the more slowly, bioabsorbing filament walls. Put otherwise, a scaffold polymer may have a variable or gradient of bioabsorptive rate from luminal interior to the scaffold exterior. Thus, interior i.e., luminal, polymer bioabsorptive or bioabsorption rates are higher than exterior or externally-disposed polymer bioabsorptive rates.

Bioabsorbable, biocompatible materials suitable for both manufacture of hollow filaments and for use as a material for filling the interior of the hollow filaments can be selected from any of a wide variety of biocompatible, synthetic, natural, and semi-synthetic materials commonly used in clinical practice and in biomedical research. The hollow filaments may be comprised of polymer(s) including poly(lactic acid), poly (glycolic acid), poly(trimethylene carbonate), poly(dimethyltrimethylene carbonate), poly(amino acids)s, tyrosine-derived poly(carbonates)s, poly(carbonates)s, poly(caprolactone), poly(para-dioxanone), poly(esters)s, poly(esteramides)s, poly(anhydrides)s, poly(ortho esters)s, collagen, gelatin, serum albumin, proteins, polysaccharides, mucopolysaccharides, carbohydrates, glycosaminoglycans, poly (ethylene glycols)s, poly(propylene glycols)s, poly(acrylate esters)s, poly(methacrylate esters)s, poly(vinyl alcohol), and copolymers, blends, and mixtures of said polymers as well as oligomers containing bioabsorbable linkages that are block-copolymerized with otherwise non-degradable polymers that are metabolizable or excretable upon release by hydrolysis or degradation of said bioabsorbable linkages. Surface modification, graft polymerization, copolymerization, or blending of the bioabsorbable materials of this invention with growth factors, cell attachment binding site moieties, and cell signaling molecules may be advantageous for improved cell attachment and/or improved cell function, aggregation, or initiation of the follicle neogenesis process.

Naturally occurring polymers (or biopolymers, or biomaterials) suitable for use as hollow filaments or as filling materials for hollow filaments include collagen, gelatin, cellulose derivatives, starch, dextrin, chitosan, lipoproteins, recombinant human forms of collagen and gelatin, fibrinogen, fibrin, fibronectin, laminin, albumin, other serum proteins, polysaccharides, mucopolysaccharides, and other biopolymers that naturally occur in the human body. Suitable biopolymers can be used either in native form or in modified form such as by crosslinking with toxicologically acceptable crosslinking agents e.g., to reduce solubility. The filling material can be utilized in a variety of physical forms including fibers, gels, and porous structures. For example, cells can be combined with a solution of fibrinogen, which can then be converted into a bioabsorbable gel upon exposure to thrombin.

Another approach involves the use of a copolymer of ethylene oxide and propylene oxide known as Pluronic™ F-127, which is commercially available from BASF Corp., Mount Olive, N.J. This surfactant is compatible with living cells and above a critical concentration forms a gel when warmed to body temperature from cooler temperatures. Thus the hollow filament can, for example, first be treated with a solution of Pluronic™ F-127 in alcohol followed by evaporation of the alcohol to impart a hydrophilic coating on its lumenal surfaces. A cold solution of Pluronic™ F-127 containing a suspension of cells can then be wicked or injected into the lumen of the filament and placed in a warm environment to gel the Pluronic™ F-127 and prevent the cells from being dislodged from the filament. Other biocompatible gel-forming materials include collagen, gelatin, serum albumin, Matrigel™ basement membrane matrix (BD Biosciences, San Jose, Calif.) and various polyethylene glycol molecules with end groups that covalently react to form gel networks.

Other uses for the structures of the present invention are envisioned. For example, by simply bundling together a large number of hollow filaments, with or without the addition of other ingredients, it is possible to obtain a three dimensional object as the finished product with continuous pores running through it. Such structures are useful in the field of tissue-engineered cartilage. Because cartilage is essentially avascular, scaffolds used for tissue-engineered cartilage suitably have an interior that is readily accessible to nutrients. Moreover, the seeding of such scaffolds is facilitated by pores coursing directly through the device. In addition, by orienting the pores along the axis of the biomechanical load, seeded chondrocytes will be stimulated to respond appropriately and organize into the columnar architecture of native articular cartilage.

Hyaluronic acid is known to be a useful biomaterial for tissue engineering applications and is suitable for the above-mentioned scaffolds for tissue engineered cartilage. A suitable material is obtained by self crosslinking hyaluronic acid with a condensing agent, suitably EDC as described by K. Tomihata and Y. Ikada, "Crosslinking of hyaluronic acid with water-soluble carbodiimide", *J. Biomed. Mater. Res.*, 37, 243-251 (1997), the teachings of which are incorporated by reference herein. Alternatively, hyaluronic acid can be crosslinked by a variety of other approaches including methods described in "Modification of Natural Polymers: Hyaluronic Acid" by Y. Luo, K. R. Kirker, and G. D. Prestwich, Chapter 45 in *Methods of Tissue Engineering*, A. Atala and R. P. Lanza, eds., Academic Press, 2002, pp. 539-553, the teachings of which are incorporated herein.

Alternatively, hyaluronic acid can be converted into an insoluble material for use in the present invention by esterification, as described in U.S. Pat. No. 4,851,521, "Esters of Hyaluronic Acid", by Francesco della Valle and Aurelio Romeo (Jul. 25, 1989), the teachings of which are incorporated herein. A suitable material of this type is the benzyl ester of hyaluronic acid. While trans-esterification is a suitable method of crosslinking because the resultant product is converted back into soluble hyaluronic acid upon hydrolysis of the ester linkages within a few days in vivo, other crosslinking agents and added crosslink-forming molecules also can be employed. Amine terminated crosslinking molecules are also suitable, including, but not limited to, aliphatic diamines, diaminoacid esters such as alkyl esters of lysine, and amine-terminated poly(ethylene glycol).

Many of the chemical methods of crosslinking hyaluronic acid also can be used to facilitate covalent attachment of bioactive molecules to the hylauronic acid structure to enhance the performance of the resultant scaffold. For example, peptides containing the cell attachment domain sequence of amino acids Arg-Gly-Asp (RGD) can be used to enhance cell attachment to the crosslinked hyaluronic acid scaffold.

In the use of hyaluronic acid to manufacture scaffolds for tissue engineered hair follicles it may be desirable to attach growth factors and angiogenesis factors to the scaffold is such a way as to be released during degradation of the scaffold for encouraging blood vessels to grow into the newly forming follicle or for other beneficial purposes. In addition to covalent attachment of small molecules to the scaffolds, higher molecular weight molecules such as proteins, glycoproteins, and other biopolymers, such as collagen, laminin, fibronectin, and the like, can be physically or electro-statically bound into the structure to provide greater physical integrity, cell attachment capacity, or bioactivity. Other glycosaminoglycans including chondroitin sulfate, heparin, dermatan sulfate, versican, and the like also can be used advantageously in the present invention in place of hyaluronic acid.

A suitable material for manufacture of scaffolds for tissue engineered hair follicles is chondroitin-6-sulfate. The surprisingly beneficial effect of chondroitin-6-sulfate on the process of follicle neogenesis is illustrated in Example 6. A suitable composition is a mixture of chondroitin-6-sulfate and gelatin, crosslinked with EDC, and rendered microporous with the use of sebacic acid particles as a porogen, as illustrated in Example 9, or by conversion into a mass of fibers as illustrated in Example 10.

Hair follicle formation requires an interaction between cells of the epidermis (i.e. keratinocytes) with cells of the dermis (i.e. dermal fibroblasts or dermal/follicular papilla cells). Dermal and epidermal cells for use in the manufacture of tissue engineered living skin equivalents for use in the treatment of burn patients are often currently obtained from human infant foreskin tissue because it is readily available. These skin equivalents, although of great clinical value, are devoid of hair follicles. Thus keratinocytes generally or keratinocytes from that source have generally not been thought to have any particular value in the construction of tissue-engineered implants that are required to induce the formation of new hair follicles. It has been stated that, "[p]referably the epidermal cells are from the same patient being treated . . . " in the disclosure by Cooley and Vogel (WO 99/01034), the teachings of which are incorporated herein.

Surprisingly, it has been discovered here that keratinocytes from the adult scalp are not particularly reliable and that keratinocytes from the infant foreskin are, in fact, more effective in their ability to induce follicle neogenesis in combination with dermal papilla cells. While the reason for this finding is unknown (and not wishing to be bound by any particular theory), we believe that epidermal stem cells, a very small subpopulation of epidermal keratinocytes, are required to initiate follicle neogenesis and that infant epidermis is a richer source of these cells than adult epidermis. Other sources of stem cells from the infant, therefore, also could be useful. For example, blood obtained from the umbilical cord could be a source of useful stem cells, as could cells obtained from embryos or established embryonic stem cell lines, or cells obtained from infant scalp skin under established organ donor procedures.

The dermal component of the epidermal/dermal cell construct of the present invention can be obtained from dissected follicles obtained from the subject who is to receive the hair restoration treatment. Another possibility, however, is to obtain cells from the scalp of an organ donor, suitably an infant. Cells that are to be seeded into a scaffold can be obtained by culture of a follicle fragment selected from fragments comprising the dermal papilla, dermal sheath, matrix, and inner and outer root sheaths. Alternatively, cells can be simply cultured from a mixture of cells prepared from the intact scalp dermis or from scraps of dermal and follicular tissue remaining after follicular unit dissection of donor site tissue from a traditional hair restoration surgical procedure in which the donor is also the recipient of said cells.

Epidermal cells, regardless of their origin, are suitably contained within the lumen of the hollow filament, adherent to or adjacent to the lumen interior wall or otherwise contained in a porous structure therein. Hair follicle progenitor cells obtained from a biopsy of hair bearing scalp, and multiplied in culture, from the person who is to receive the biomimetic grafts are suitably contained primarily in the proximal compartment of the filament lumen, which corresponds to the bulb of a hair follicle. Thus the graft is self-contained in that both dermal and epidermal components are present in the correct relationship to each other, obviating the need for implanted cells to interact with the intact epidermis or epidermal cells that grow down the implanted graft. This, in turn, provides reliability and reproducibility of new hair follicle formation.

Figure 12:
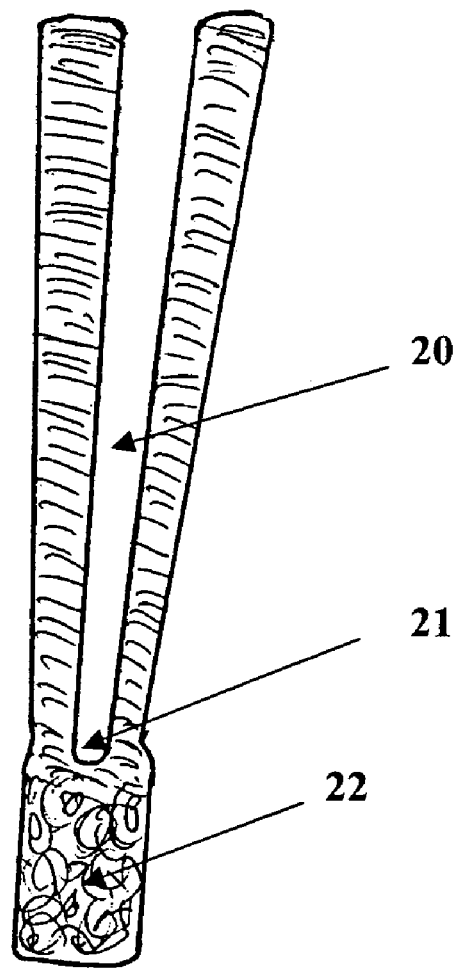
FIG. 12 is a cross-sectional schematic representation of a hollow filament of the present invention in which the lumen (20) is slightly tapered to a closed end (21) attached to a porous plug (22).
Figure 13:
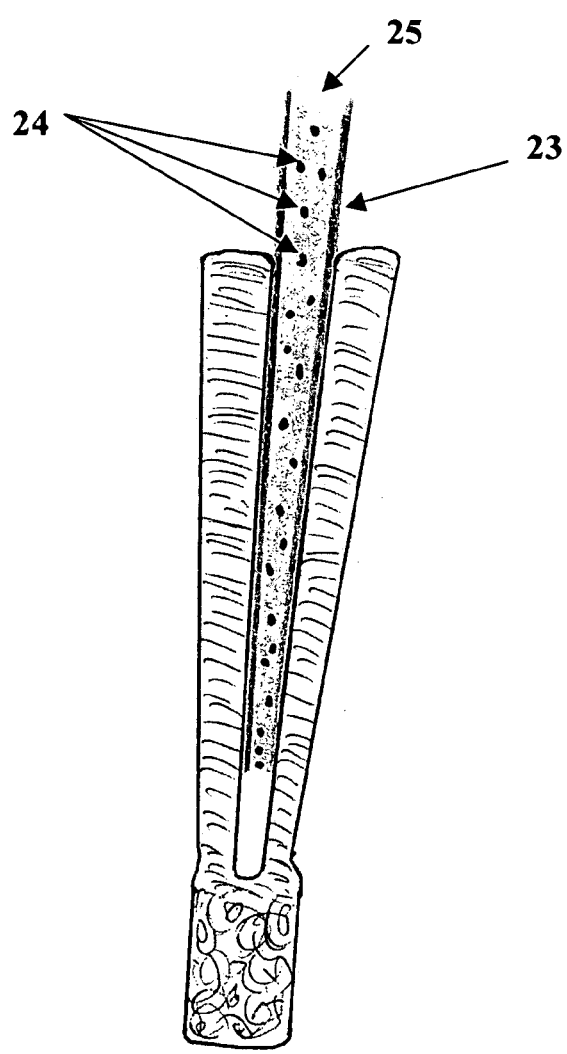
FIG. 13 is a cross-sectional schematic representation of a hollow filament of the present invention showing a fine pipette tip (23) containing cells (24) and fluid (25) that has been inserted into the tapered lumen (20).
Figure 14:
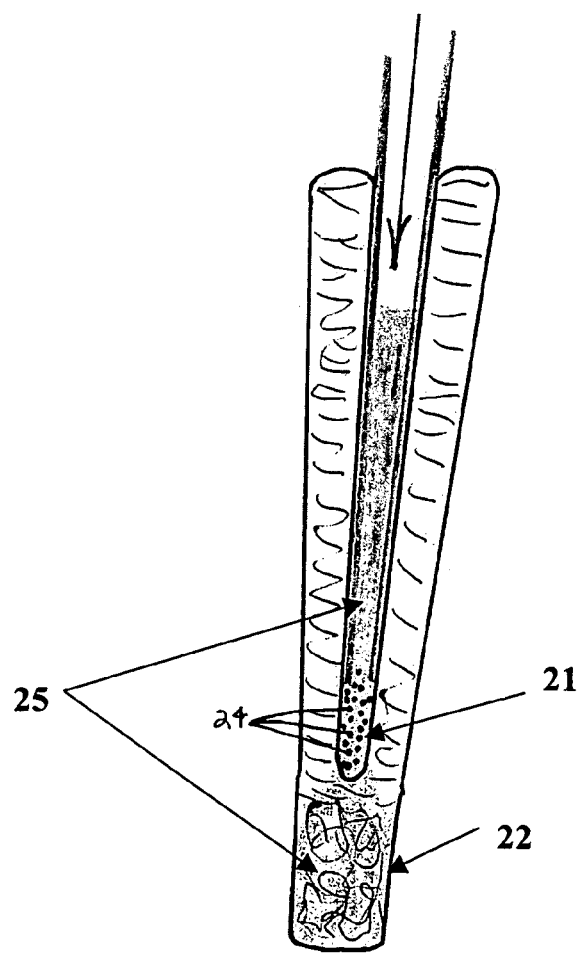
FIG. 14 cross-sectional schematic representation of a hollow filament of the present invention showing a suspension of fluid (25) and cells (24) being expelled from a pipette tip (23) whereby the cells collect in the closed end of the lumen (21) and the fluid (25) is fully absorbed in the porous plug (22).

Alternatively, dermal and epidermal cells can be combined as a mixture, with the optional addition of stem cells, and seeded into the scaffold just prior to implantation. In this case the cells would associate and reorganize in situ. A suitable scaffold configuration for this method of cell delivery is shown in FIGS. 12 through 14. In this embodiment, the scaffold is manufactured as a hollow filament with one end closed to form a porous, sponge-like structure that serves as a reservoir to absorb fluid. Thus upon injection of a suspension of cells and fluid into the lumen of the hollow filament, the fluid is wicked into the reservoir end causing collection of the cells into a concentrated area at the closed end of the filament. The scaffold containing cells is then immediately implanted into a stab wound in the skin in the same manner that follicular grafts are implanted in a traditional hair restoration surgery procedure. A process for manufacturing the scaffold of this embodiment is illustrated in Example 9 and comprises the following steps:

1. Provide a tapered mandrel with the same dimensions as the distal segment of a pipette tip or other suitable fluid delivery means.
2. Provide a mold cavity, open at both ends, that accommodates the mandrel of step 1 as an insert for the cavity, which is longer than the mandrel, the extra length creating a void volume approximately equal to the volume of the mandrel itself.
3. Provide a mixture of bioabsorbable materials A dissolved in solvent B and porogen particles C that are soluble in solvent D, but not in solvent B.
4. Fill the cavity of step 2 with the mixture of step 3 and insert the mandrel of step 1.
5. Remove solvent B and extract the molded part from the mold cavity.
6. Place the molded part of step 5 into a solvent D to remove the porogen particle.
7. Place the molded part of step 6 into a solution of crosslinker E dissolved in solvent F.

8. Rinse with fresh solvent F or other suitable solvent and allow the resultant scaffold to dry.
9. Optionally re-hydrate the scaffold of step 8 with an aqueous solution of a water-soluble substance G and allow the water to evaporate to create a protective coating.
10. Prepare a solution of bioabsorbable material H in solvent I.
11. Coat the scaffold of step 9 with the solution of step 10 and allow solvent I to evaporate.
12. Remove the protective coating of material G by soaking the scaffold in water, rinsing with fresh water, and allowing the water to evaporate.

In a suitable process involving the above steps, A is a mixture of chondroitin-6-sulfate and gelatin, B is water, C is sebacic acid particles less than 63 microns, D is acetone, E is EDC, and F is a 9:1 mixture by volume of acetone:water.

A modification of the above process to create the embodiment illustrated in Example 10 comprises the following steps:
1. Provide a tapered mandrel with the same dimensions as the distal segment of a pipette tip or other suitable fluid delivery means except that the tip of said mandrel is extended slightly to provide a sharp point.
2. Coat the mandrel of step 1 with a water-soluble polymer A.
3. Attach to the tip of the mandrel of step 1 a permeable, bioabsorbable filtration substance B that is suitable for separation of cells from a suspension of cells in fluid, said filtration substance being substantially encased in a removable protective coating C soluble in solvent D.
4. Coat the entire mandrel and said filtration substance B with a film-forming bioabsorbable polymer E dissolved in solvent F.
5. Remove solvent F of step 4 to create a continuous layer of bioabsorbable polymer film covering the mandrel and attached tip of step 3.
6. Create an opening in the film of step 5 by removing a small piece of said film covering the filtration material distal to its point of attachment to the mandrel.
7. Substantially remove polymer A by soaking the product of step 6 in water.
8. Substantially remove the protective coating material C by soaking in solvent D.
9. Remove the mandrel from the product and continue steps 7 and 8 as necessary to fully remove materials A and C.

In a suitable embodiment of the above process, A is a surfactant, for example Pluronic™ F-127, B is a mass of fibers comprised of chondroitin-6-sulfate and cross-linked gelatin, C is caramelized cane sugar, D is water, E is PLGA, and F is dichloromethane.

A suitable method for manufacturing long hollow filament scaffolds of the present invention that are open at both ends involves the use of nylon monofilament as a mandrel, subsequently removed by dissolution, upon which the various ingredients are deposited. Fibers made from other materials that can be removed without damaging the biomaterial investments are also envisioned as being useful in this process. Alternatively, hollow filament melt extrusion is a proven technology that also can be used to create the hollow filaments of the present invention.

In a process of the present invention, a fine nylon fiber is first coated with particles to ensure that application of a bioabsorbable material in the form of a viscous solution will adhere to the fiber. These particles are applied to, adhered to, or associated with, the nylon fiber using a solution of nylon or other polymers such as polystyrene. The nylon (or other polymer) particles firmly adhere to the fine nylon fiber and assist the subsequent coating of the fiber with a viscous, aqueous solution, for example a solution of hyaluronic acid, which otherwise would not cling to the nylon surface. A suitable substance for use as particles is sebacic acid, which is substantially insoluble in water (a solvent for hyaluronic acid) and TFE (a solvent for nylon), but is freely soluble in acetone (a non-solvent for hyaluronic acid and nylon). The particles also serve to impart a porous lumenal surface on the resultant hollow filament upon removal of said particles. After curing, crosslinking, or otherwise rendering the coated bioabsorbable material insoluble in water, the nylon and the particles attached to the nylon are removed with the appropriate solvents. If desired, an additional coating of a different bioabsorbable material may then be applied. At this stage of the process, with the nylon and nylon-bound particles removed, a wider choice of solvents can be used to apply this second material. A suitable second material is a copolymer of lactide and glycolide (hereinafter referred to as PLGA), thereby providing in this process a hollow filament with a HAX interior and a PLGA exterior.

From the above, the detailed steps of this process are:
1. Provide a water-soluble material W.
2. Provide a fiber of material X that is soluble in solvent A.
3. Provide bioabsorbable material Y that is soluble in solvent B.
4. Provide particles P that are soluble in solvent C.
5. Provide bioabsorbable material Z that is soluble in solvent D.
6. Provide a polymer M that is soluble in solvent N.
7. Prepare a solution of polymer M in solvent N.
8. Coat the fiber of step 2 with the solution of step 7.
9. Coat the particle P of step 4 onto the coated fiber of step 8 and allow solvent N to evaporate, thereby bonding said particles onto said fiber.
10. Prepare a solution of material Y in solvent B.
11. Coat the solution of step 10 onto the particle encrusted fiber of step 9 and allow solvent B to evaporate.
12. If material Y is water soluble, render material Y water insoluble by crosslinking.
13. Remove polymer M from the coated fiber of step 12 by dissolution and rinsing with solvent N.
14. Remove the particles P from the coated fiber of step 13 by dissolution and rinsing with solvent C.
15. Remove the fiber X from the coated fiber of step 14 by dissolution and rinsing with solvent A.
16. Prepare a solution of material W in water.
17. If required, apply a protective coating of the solution of step 16 to the filament of step 15 and allow the water to evaporate.
18. Prepare a solution of bioabsorbable material Z in solvent D.
19. Coat the fiber of step 17 with the solution of step 18 and allow solvent D to evaporate.
20. Remove the protective coating of material W by soaking the filaments in water, rinsing with fresh water, and allowing the filament to dry.
21. Cut the filaments into the appropriate lengths and sterilize.
22. Seed the filaments with the appropriate cells by allowing a suspension of the cells in the appropriate volume of the appropriate fluid to wick into the lumen of the filament.
23. Optionally load the filament with additional cellular constructs by inserting into one end of the filament.
24. Make an incision in the skin where the growth of a hair shaft is desired and implant the filament of step 22 or 23 into the incision with the end containing a cellular construct imbedded in the skin and the distal end extending percutaneously above the skin.

In a suitable process involving the above steps, W is caramelized cane sugar, X is nylon, A is TFE, Y is hyaluronic acid (sodium salt), B is water, P is sebacic acid (particle size 10 to 500 microns, preferable 50 to 200 microns), Z is PLGA, D and N are dichloromethane, M is polystyrene, and C is acetone. If desired to impart porosity to the PLGA, D can be specified as a solution of glycerol and TFE. Upon evaporation of the TFE, the PLGA and glycerol phase separate into a bicontinuous emulsion. Removal of the glycerol by dissolution in water imparts a microporous structure to the residual PLGA coating.

In order to manufacture a scaffold for use in cartilage tissue engineering applications, a large number of the fibers of step 11 above, with or without the addition of other ingredients, can be bundled together using additional coating solution of step 10 as an adhesive. Prior to dissolving the mandrel fibers the bundle can be cut into discs from which the desired products can be constructed after dissolving the fibers and completing the processing steps.

EXAMPLES

Example 1

PLGA Does Not Impair Transplanted Follicle Survival and Hair Growth

Figure 7:
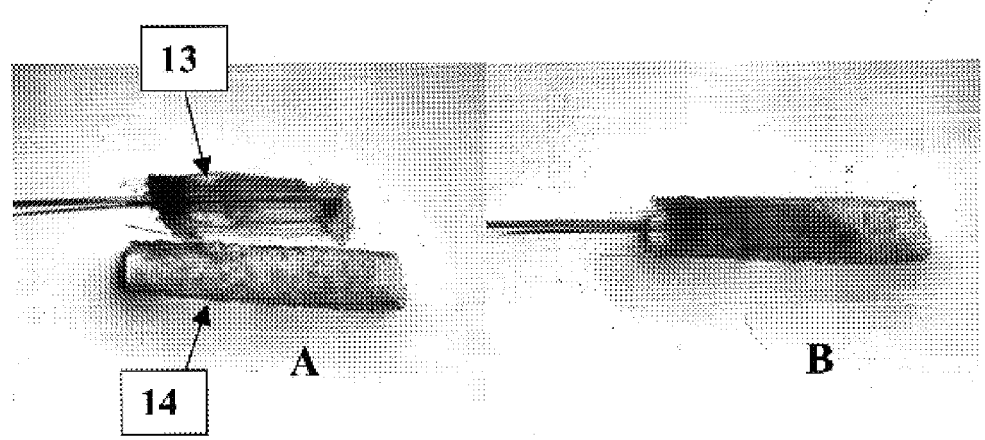
FIG. 7(A) is a photograph of a mouse vibrissa (whisker) follicle (13) and a PLGA hollow filament (14) with an inside diameter of sufficient size to accommodate the excised follicle.
FIG. 7(B) is a photograph of the PLGA hollow filament of FIG. 7(A) with the follicle (13) inserted into the lumen.

A copolymer (PLGA) of d,l-lactide and glycolide (52:48) was obtained from CCA Purac Biochem by, Gorinchem, The Netherlands (Purasorb® PLGA, inherent viscosity 1.06 dl/g in chloroform) and dissolved in dichloromethane (10% w/v). Cane sugar was melted and heated until caramelized and allowed to cool to the point that filaments of the desired size could be pulled from the melt. The filaments were cooled until solidified and then immediately placed on a surface covered with powdered sodium chloride to prevent them from becoming sticky. Hollow filaments were prepared by coating the PLGA solution onto the filaments of powdered, salt-encrusted caramelized sugar. The dichloromethane was evaporated, and the sugar and salt were dissolved and removed by placing the coated filaments in water. Vibrissa (whisker) follicles were excised from euthanized C57B16 mice (Charles River) at Mercer University (Atlanta, Ga.) under an IACUC-approved. The excised whiskers were reimplanted into oblique incisions on the shaved dorsal skin of syngeneic mice. This procedure was then repeated with the excised follicles first inserted and snugly fit into the lumen of the hollow PLGA filaments such that the follicles were completely surrounded by the polymer (FIG. 7). After 30 days the implanted mice were euthanized and the skin excised, stretched over rectangles of cardboard, fixed in formalin and processed by routine methods of paraffin embedding, sectioning, and H&E staining for analysis by light microscopy.

Figure 8:
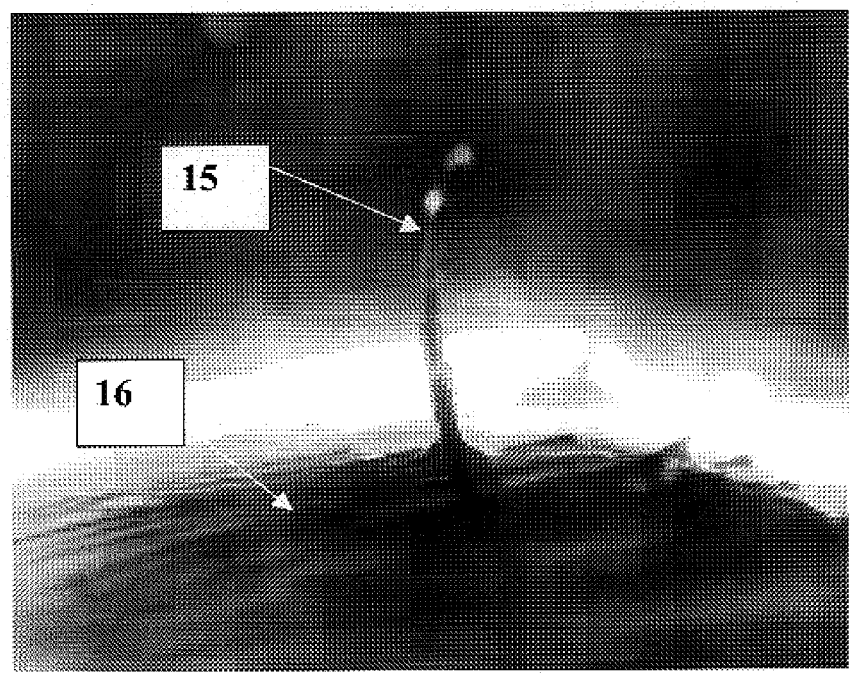
FIG. 8 is a photograph of a mouse whisker (15) that was observed growing on the back of a mouse against the background of regrown shaved pelage hair (16) 30 days post-implantation of a vibrissa follicle contained in a PLGA hollow filament.

After 30 days 7 out of 8 control follicle implants were found to be growing vibrissa hair shafts. 2 out of 3 PLGA/follicle implants also were found to be growing hair shafts as well (FIG. 8). Histology did not reveal any abnormalities in the regenerated, transplanted follicles with or without ensheathment in PLGA.

Example 2

Preparation of Microporous PLGA Hollow Filament

Figure 4:
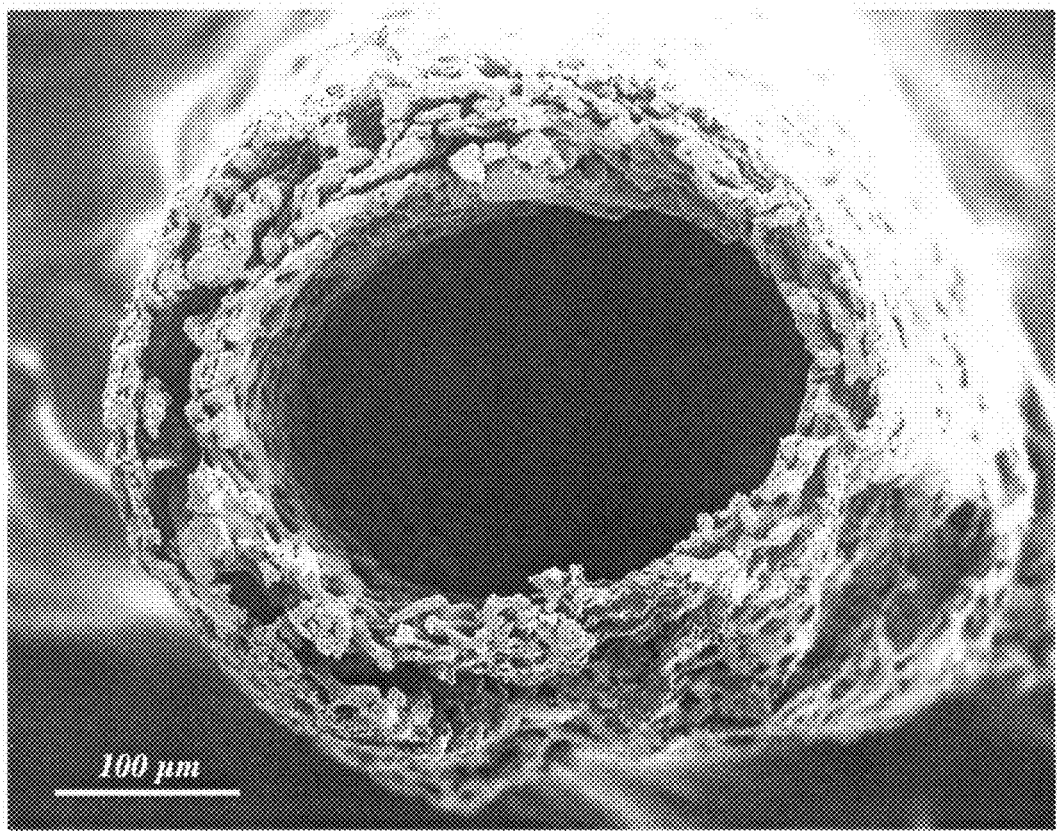
FIG. 4 is a scanning electron micrograph (SEM) of a hollow filament of the present invention made of a porous copolymer of d,l-lactide and glycolide (PLGA).
Figure 5:
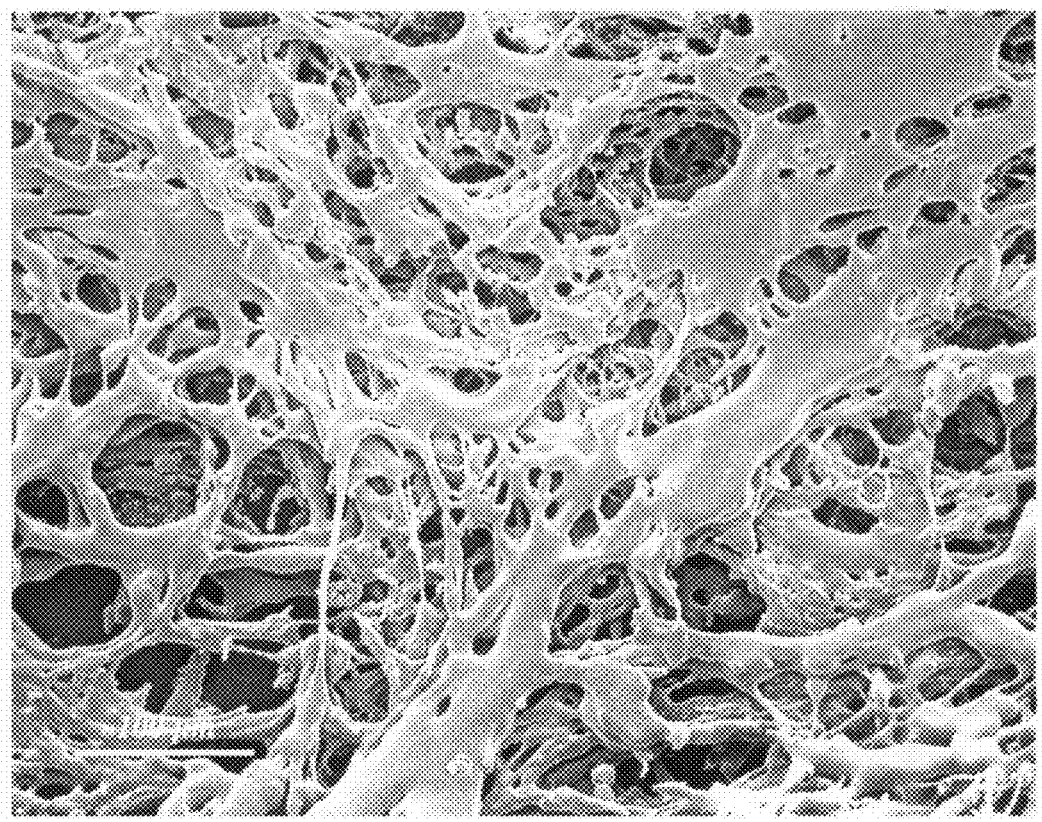
FIG. 5 is an SEM of the porous inner surface of the hollow filament of FIG. 4, which was exposed by cutting open the tube.
Figure 6:
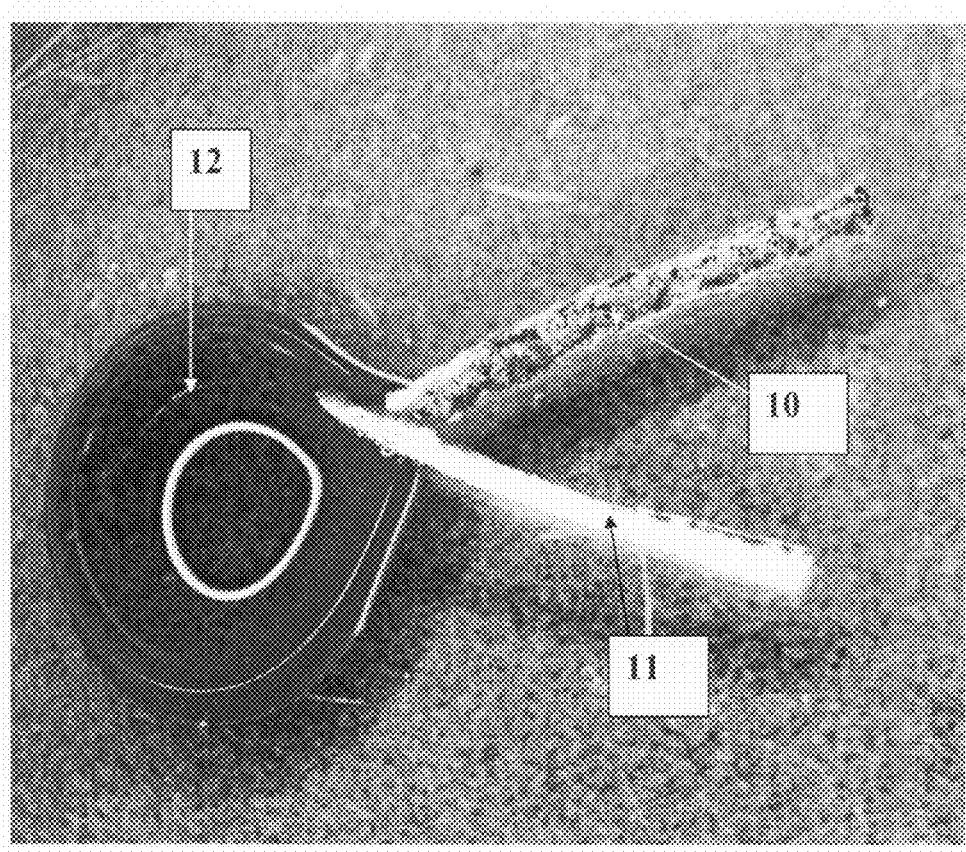
FIG. 6 is a light photomicrograph (in black & white) showing a filament (10) with the construction shown in FIG. 1 wherein the outer filament (1) is made of solid PLGA and the porous inner filament (2) is made of crosslinked hyaluronic acid (HAX).

A solution of glycerol (glycerine U.S.P.) and PLGA (Resomer™ RG504, Boehringer Ingelheim, Germany) was prepared in TFE (Aldrich Chemical Co., Milwaukee, Wis.) such that the ratio of glycerol to PLGA was 80:20 (w/w). This solution was coated onto caramelized cane sugar filaments (prepared as described above in Example 1) in several layers with time allowed between coats for drying. Evaporation of the TFE, a solvent for both glycerol and PLGA, caused the concentration of the solutes to increase until glycerol no longer remained miscible. Phase separation of glycerol from the PLGA/TFE resulted in the formation of a bicontinuous emulsion. The coated filaments were then placed in water, which caused the sugar and the glycerol, as well as any residual TFE, to dissolve rapidly and leach out of the now micro-porous PLGA. The resultant porous hollow filaments were rinsed with water and allowed to dry completely in a desiccator. The porous structure of the dry PLGA hollow filaments is shown in the SEM photographs presented in FIGS. 4 and 5.

Example 3

Preparation of a Hydrophilic PLGA Hollow Filament

A solution of approximately 5% (w/v) Pluronic™ F-127 surfactant (Sigma Chemical Co., St. Louis, Mo.), which is a copolymer of ethylene oxide and propylene oxide, was prepared in anhydrous ethanol with gentle heating. Hollow filaments of PLGA were prepared as described in Example 1. The clear, colorless solution of Pluronic™ F-127 was allowed to wick into one of the PLGA filaments and the ethanol allowed to evaporate completely. A drop of red food coloring dye was placed on a glass plate. A 15 mm length of the Pluronic™ F-127-treated PLGA hollow filament and a 15 mm length of the untreated control filament of the same diameter were contacted with the dye by touching one end of each filament to the surface of the liquid. The Pluronic™ F-127-treated filament rapidly wicked the aqueous dye solution through its entire length whereas the untreated filament only slowly wicked the dye into 4 mm of its length.

Example 4

Preparation of a PLGA Coated HAX Filament

Sebacic acid (Aldrich Chemical Co., Milwaukee, Wis.) was ground by mortar and pestle and sieved to obtain particles >63 and <212 microns in size. A one meter length of fine monofilament nylon fiber (0.003-inch diameter, Shakespeare Monofilament Division, Columbia, S.C.) was coated with a solution of nylon in TFE (10% w/v) and immediately encrusted with the sebacic acid particles by drawing the fiber through a pipette containing the solution and then through a pile of the sebacic acid particles placed at the exit of the pipette tip. The fiber was suspended at one end and allowed to hang in a vertical position. A solution of hyaluronic acid sodium salt was made by combining 180 mg of sodium hyaluronate powder (1.4 million molecular weight, Lifecore Biomedical, Chaska, Minn.) with 10 ml of water and allowing this to hydrate and dissolve at room temperature overnight. The solution was mixed well and then coated onto the fiber by manually running a bead of the gelatinous liquid down the fiber. The thin coating of hyaluronate solution was allowed to dry and then two additional coats were applied with time allowed between coats for drying. The fiber was then cut into approximately 4-cm lengths and placed in a vial containing 0.2% (w/v) of N,N'-isopropylethylaminocarbodiimide (Sigma Chemical Co., St. Louis, Mo.) in acetone containing 10% (v/v) water. After 3 hours at room temperature, the solution was decanted and replaced with pure acetone. The acetone was decanted and residual acetone removed by evaporation. The vial was then filled with TFE (Aldrich Chemical Co., Milwaukee, Wis.) and allowed to stand overnight at room temperature. The TFE was decanted and replaced with fresh TFE and after several hours this was decanted and replaced with acetone. The acetone was decanted and residual acetone removed by evaporation to yield HAX filaments.

Cane sugar was heated over an open flame in a test tube with stirring until it melted and caramelized. The dark brown melt was poured out and allowed to solidify. A syrup was prepared by dissolving this in water (approximately 20% w/v). The dry HAX filaments were placed in the syrup whereupon they rapidly absorbed the liquid and became noticeable larger in diameter. The filaments were removed from the syrup and allowed to dry partially. They were then coated with powdered sodium chloride (<63 microns) and placed in a desiccator to dry overnight. The stiff, brittle, amber colored filaments were dipped into a 10% (w/v) solution of PLGA (Purasorb® PDLG, inherent viscosity 1.06 dl/g in chloroform, CCA Purac Biochem by, Gorinchem, The Netherlands) in dichloromethane (Aldrich Chemical Co., Milwaukee, Wis.) and the solvent allowed to evaporate. The coated filaments were then allowed to soak in water until the sugar and salt dissolved, as evidenced by the loss of the amber color. The filaments were then returned to the desiccator and allowed to dry completely. Control hollow filaments of PLGA not containing HAX were prepared by the method of Example 1. The ability of these filaments to wick aqueous fluid was tested by dipping one end into a drop of water containing red food coloring dye. The red colored water rapidly entered the lumen of the filament containing HAX and filled it completely, thereby imparting a red color to the filament. The filament not containing HAX, however, did not wick water and, being water repellant, floated on the surface of the water.

Example 5

Figure 9:
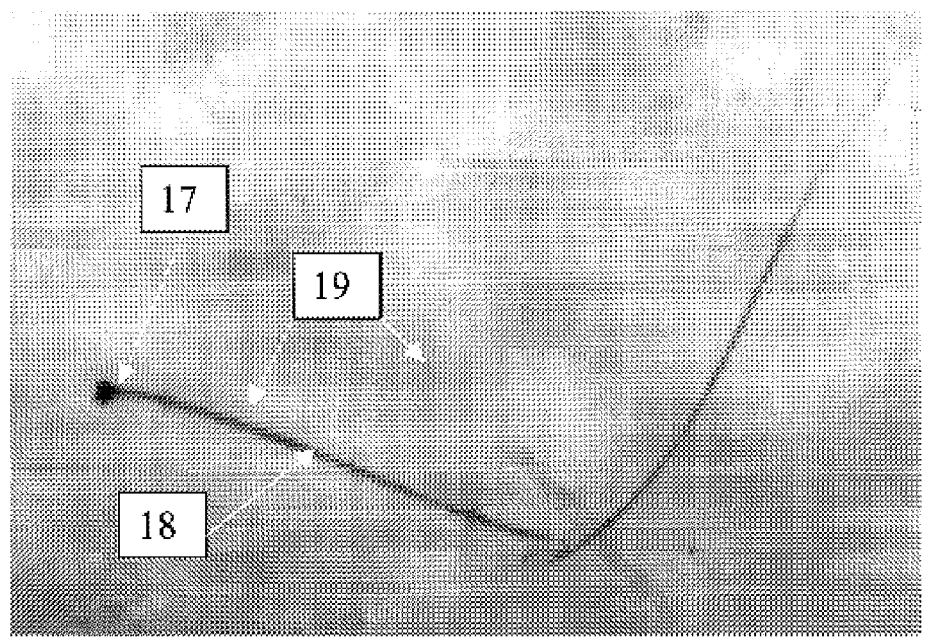
FIG. 9 is a photomicrograph of a hair follicle bulb (17) and hair shaft (18) growing under the skin of a mouse 30 days post-implantation of a mixture of cells obtained from neonatal mouse skin contained in a PLGA hollow filament (19).

Hair Follicle Neogenesis and Hair Shaft Growth in Vivo from Mouse Cells Contained in a PLGA Hollow Filament Scaffold Epidermal and dermal cells were isolated from newborn mouse pups as previously described (S. M Prouty, L. Lawrence, et al. (1996). "Fibroblast-dependent induction of a murine skin lesion with similarity to human common blue nevus." *Am J Pathol* 148(6): 1871-85), the teachings of which are incorporated herein. Two deviations from the published procedure were the use of C57/B16 mice (Charles River Laboratories) and the use of dispase (Gibco), rather than trypsin, to facilitate separation of the epidermis from the dermis of the neonatal mouse skin. Once both populations of cells, dermal and epidermal, were separately isolated they were recombined so that the ratio of dermal cells to epidermides, also known as epidermal buds, was 100:1. This cell combination was then spun down at 900 rpms for 5 minutes. The resultant pellet was resuspended in PBS to obtain a cell concentration of at least 10 million total cells per milliliter and promptly loaded into PLGA hollow filaments, prepared according to the method discussed in Example 1, by simply submerging the fiber in the suspension of cells. These cell-seeded filaments were then implanted underneath the dorsal skin of a nude (Nu/Nu) mice by puncturing the skin with a 19-gauge hypodermic needle, withdrawing the needle until half of the open bevel was exposed, inserting the hollow filament implant into the opening, and then withdrawing the needle completely while pushing the filament under the skin. At three weeks post-implantation the mice were necropsied and the skin excised. Follicle-like structures and hair shafts were observed associated with the PLGA scaffold material on the subcutaneous side of the skin at the site of filament implantation. As shown in FIG. 9, a well-formed hair follicle bulb and long hair shaft can be seen in this photomicrograph. The scaffold material is difficult to visualize because it is colorless and partially degraded.

Example 6

Use of Chondroitin-6-Sulfate as Additive in Cell Suspension

Figure 10:
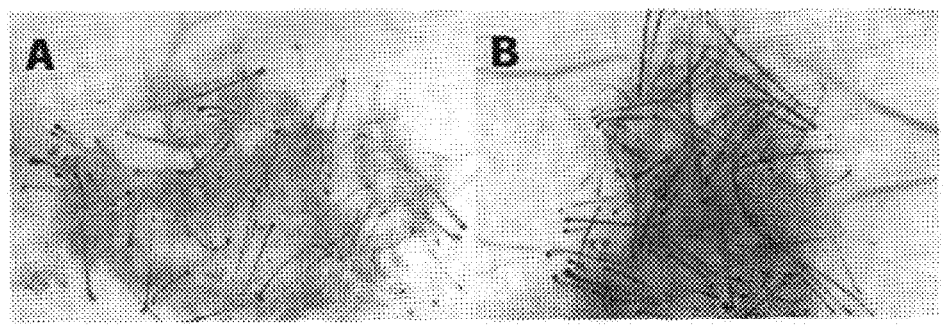
FIG. 10 is a side-by-side comparison of two photomicrographs taken at the same magnification of the underside of skin excised from a nude mouse that had been injected 13 days previously with cells obtained from newborn black mouse epidermis and dermis. Panel A shows the control injection site and panel B shows the injection site containing exactly the same number of cells except that the injection fluid also contained 5% (w/v) of condroitin-6-sulfate, which resulted in the neogenesis of hair follicles that are larger and more numerous than the control.

The methods described in Example 5 were utilized to evaluate a number of soluble materials added to the suspension of cells prior to injection into the nude mouse. Exactly the same number of each cell type was injected in both control and test material injection sites, which were located on the same mouse. As shown in FIG. 10, the follicles formed in the subcutaneous space at 13 days post-injection of cells were clearly larger at exactly the same magnification in the presence of an initial 5% concentration of chondroitin-6-sulfate (Sigma Chemical Co., St. Louis, Mo.).

Example 7

Use of Pluronic™ F-127 as Additive in Cell Suspension

Figure 11:
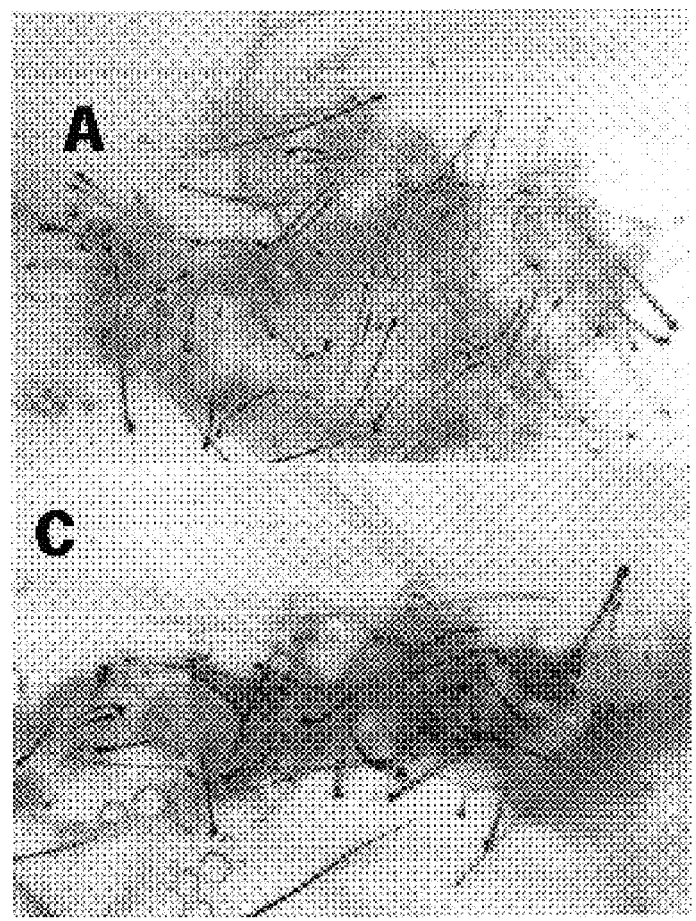
FIG. 11 also is a side-by-side comparison of two photomicrographs taken at the same magnification of the underside of skin excised from a nude mouse that had been injected 13 days previously with cells obtained from newborn black mouse epidermis and dermis. Panel A shows the same control injection site of FIG. 10 and panel C shows the injection site in the same mouse containing exactly the same number of cells except that the injection fluid also contained 20% (w/v) of Pluronic™ F-127 surfactant (a copolymer of ethylene and propylene oxides), which resulted in the neogenesis of hair follicles that are larger than those in the control.

The experiment of Example 6 was repeated with the substitution of 20% Pluronic™ F-127 surfactant (Sigma Chemical Co., St. Louis, Mo.) for the chondroitin-6-sulfate. As shown in FIG. 11, the follicles formed in the subcutaneous space at 13 days post-injection of cells were clearly larger at exactly the same magnification than the follicles in the control injection site where no Pluronic™ F-127 surfactant was present in the injected fluid.

Example 8

Preparation of Crosslinked Gelatin Hollow Filaments

Porcine skin gelatin (300 bloom, Sigma Chemical Co., St. Louis, Mo.) was dissolved in warm water to give a 5% (w/v) solution. This solution was applied to a fine nylon filament encrusted with sebacic acid particles as described in Example 4. Several coats were applied with time allow between applications for the coatings to dry. The fiber was then cut into approximately 4-cm lengths and placed in a vial containing 0.2% (w/v) of EDC (Sigma Chemical Co., St. Louis, Mo.) in acetone containing 10% (v/v) water. After 3 hours at room temperature, the solution was decanted and replaced with pure acetone. The acetone was decanted and residual acetone removed by evaporation. The vial was then filled with TFE (Aldrich Chemical Co., Milwaukee, Wis.) and allowed to stand overnight at room temperature. The TFE was decanted and replaced with fresh TFE and after several hours this was decanted and replaced with acetone. The acetone was decanted and residual acetone removed by evaporation to yield water-insoluble gelatin hollow filaments.

Example 9

Preparation of Crosslinked Chondroitin-6-Sulfate/Gelatin Scaffolds

Sebacic acid (Sigma Chemical Co., St. Louis, Mo.) was ground with mortar and pestle into particles that passed through a 63-micron sieve. Disposable 10 microliter pipette tips (Eppendorf epTIPS™, Brinkman Instruments, Westbury, N.Y.) were cut into three equal pieces. The proximal piece was discarded and the middle piece was packed with the sebacic acid powder. Chondroitin-6-sulfate (80 mg) and porcine skin gelatin (80 mg) were dissolved in 2.0 ml of warm water. This solution was loaded into a syringe fitted with a stainless steel tube that just fit into the larger opening of the sebacic acid filled pipette tip section. The solution was then injected into the packed sebacic acid such that air was expelled from the powder as the fluid moved through the packing. The distal piece cut from the pipette tip was then inserted into the filled piece. Excess paste that extruded out the open end was wiped off.

The assembled pieces were allowed to dry completely by storage in a desiccator overnight. They were then placed in a 0.2% (w/v) solution of EDC in 9:1 (v/v) acetone:water. After about one hour the two pieces of pipette tip were gently pulled apart and the molded product was ejected and returned to the EDC solution for an additional 3 hours, whereupon the crosslinked scaffold was soaked in pure acetone for one hour, and then allowed to dry.

Example 10

Pipette Tip Sheath Scaffold of PLGA and Crosslinked Gelatin/Chondroitin-6-Filaments Chondroitin-6-sulfate and porcine skin gelatin (100 mg each) were dissolved in 2.0 ml of warm de-ionized water and slowing injected through a 26-gauge needle into a silicone rubber tube filled with acetone that was flowing from an elevated reservoir into a beaker. The resultant fine, white filaments were collected and placed in a 0.2% (w/v) solution of EDC in 9:1 (v/v) acetone:water for about 4 hours. The filaments were then rinsed with pure acetone and allowed to dry. A solution of 30% (w/v) caramelized cane sugar in water was added to the dry filaments and allowed to soak until the filaments were completely saturated. A small tuft of the saturated fibrous mass was placed in a 1.0 mm inside diameter Teflon™ tube and allowed to dry completely in a desiccator. The cylinder of brown sugar encased filaments was ejected from the tube and mounted on the tip of a 30-gauge needle just protruding through the end of an Eppendorf pipette tip (10 microliter epTIPS™, Brinkman Instruments, Inc., USA). The pipette tip with attached sugar encased filaments was dipped into a 30% (w/v) solution of Pluronic™ F-127 in dichloromethane, allowed to dry, and then dipped into a 15% (w/v) solution of PLGA in dichloromethane and allowed to dry, with the tip suspended point down. The distal end of the dried PLGA was cut off with scissors and the entire pipette tip was placed in water. After a few minutes the PLGA film was easily slipped off the pipette tip due to the hydrated Pluronic™ F-127 surfactant coating. The resultant scaffold was allowed to soak further until all the brown color of the caramelized sugar disappeared.

Figure 15:
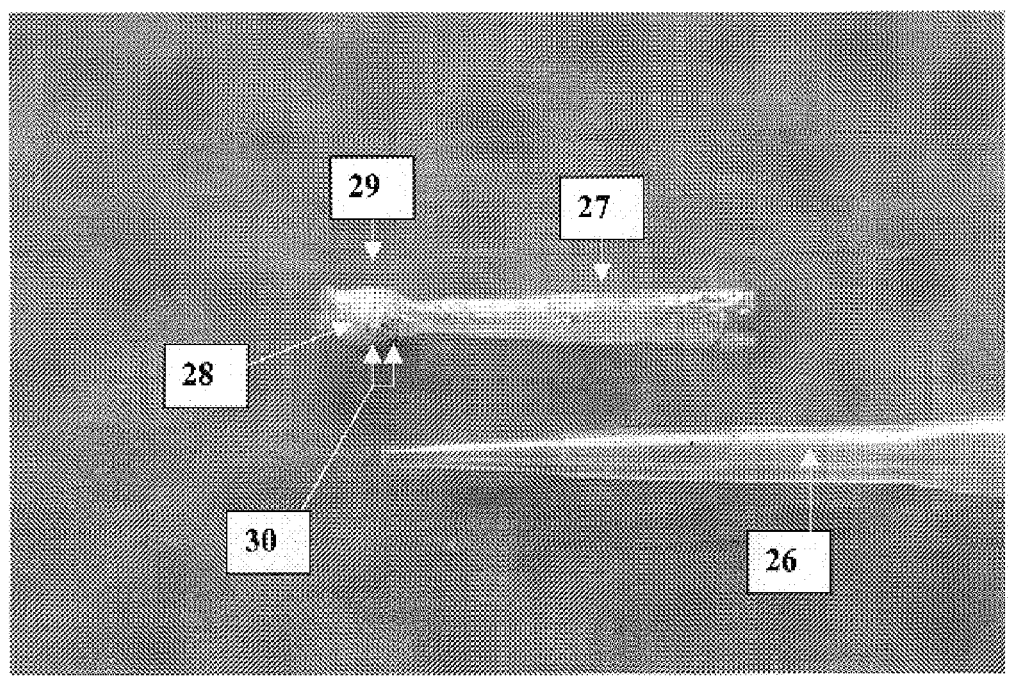
FIG. 15 is a photograph of the hollow filament scaffold of Example 10 and a 10-microliter pipette tip (26) identical to the one that was used as a mandrel in the process for making this embodiment of the present invention. The sheath (27) is made of PLGA and the fibrous mass (28) contained in the bulbous tip (29) is made of crosslinked gelatin/chondroitin-6-sulfate filaments. Charcoal particles (30) collected in the proximal portion of the fibrous scaffold upon injection of a slurry of charcoal particles and water into the scaffold through a pipette tip inserted into the scaffold sheath.

To test the ability of the fibrous material contained in the PLGA sheath to function as filtration media, and therefore as a means of collecting and implanting hair follicle inductive cells, a slurry of charcoal particles (100-400 mesh, Norit CA1 Activated Charcoal, Sigma Chemical Co., St. Louis, Mo.) in water was drawn up into a 10-microliter pipette tip, the tip inserted into the PLGA scaffold sheath, and the slurry ejected out of the pipette and out through the end of the scaffold. As shown in FIG. 15, the charcoal particles were clearly visible in the proximal end of the fibrous material where they collected as the water passed through.

Example 11

Bundled Hollow Filament HAX Scaffold for Tissue Engineered Cartilage

Sodium hyaluronate (MW $1.4 \times 10^6$ Daltons, product no. 80081, LifeCore Biomedical, Inc., Chaska, Minn. 55318) was dissolved in deionized water, placed in dialysis tubing and dialyzed against cation exchange cellulose (Dowex AG 50W-X4, purchased from BIO-RAD Laboratories, Inc., Hercules, Calif.) at 1 gram per 100 ml of deionized water and stirred by a magnetic bar at 4° C. for 2 days. The solution was removed from the dialysis tubing and freeze-dried to obtain a fluffy white solid, which was re-dissolved in deionized water to obtain a viscous solution containing 3.4% (w/v) hyaluronic acid.

Nylon monofilament thread (0.003 inches in diameter, SN-38 WonderThread™, Shakespeare Monofilament Division, Columbia, S.C.) was strung up in 3-meter lengths and coated with a slurry of sebacic acid powder (<63 microns) in a solution of approximately 5% (w/v) polystyrene (broken disposable culture dish fragments) in dichloromethane by threading the fiber through a disposable transfer pipette (cat. no. 231, Samco Scientific Corp., San Fernando, Calif.) with a portion of the bulb cut off, injecting the slurry into the pipette through the bulb opening, and then running the pipette down the length of the fiber (bulb first) such that the pipette tip acted as an orifice for uniform slurry deposition. Upon evaporation of the dichloromethane the coated fiber was flat white in color and had a noticeably rougher feel than the uncoated fiber. The above hyaluronic acid solution was then applied to the coated fiber in a similar manner. Five coats were applied with approximately one hour of drying time between the applications of each coat of hyaluronic acid. The fibers were then carefully coiled up and placed in a covered dish containing a 0.2% (w/v) solution of EDC in acetone containing 10% (v/v) deionized water and allowed to soak overnight while submersion in this liquid. They were then rinsed in pure acetone and strung up again, this time bundling approximately 10 fibers together into one continuous tow. The tow was coated with hyaluronic acid solution by hand, i.e. by holding a dab of the viscous solution between the thumb and first two fingers of one hand with the tow positioned in the gap formed at the juncture of the three digits and running the hand down the length of the tow. Several coats were applied with time allowed for drying between each application. The coated tow was then coiled and placed in a covered dish of EDC solution as above and allowed to soak overnight. It was then rinsed with pure acetone and allowed to dry.

The tow was cut into 4 cm lengths and each piece was coated with a liberal amount of hyaluronic acid solution. The coated pieces were bundled together and then lashed with 0.009-inch diameter nylon monofilament (Shakespeare) by tying individual loops around the bundle. As each loop was tightened and tied, excess hyaluronic acid solution extruded out of the bundle, which was then hung up by one end to dry. Excess solution dripped off the end and after one day the bundle was a hard, lightweight composite. It was then cut into 3 mm diameter discs with a razor blade and the discs were placed in a fresh batch of the above-mentioned EDC solution overnight both to cross-link the hyaluronic acid and to dissolve out the sebacic acid and in dichloromethane for another overnight period to finish dissolving out the polystyrene. They were then placed in TFE to dissolve out the nylon. The TFE was replaced after one hour with fresh TFE and the discs were allowed to soak in this TFE overnight. They were then rinsed with fresh TFE, then with acetone and allowed to dry. The dry discs were placed in a 50% aqueous solution of glutaraldehyde (Acros no. 41096-5000, purchased from Fisher Scientific Co., Fairlawn, N.J.) and allowed to soak for 72 hours at room temperature as recommended in "Polypeptide resurfacing method improves fibroblast's adhesion to hyaluronan strands" by M. Hu, E. E. Sabelman, S. Lai, E. K. Timek, F. Zhang, V. R. Hentz, and W. C. Lineaweaver, in *Journal of Biomedical Materials Research*, vol. 47 pages 79-84 (1999), the teachings of which are incorporated herein. This treatment converted the EDC crosslinked HAX into a slower degrading material better suited for the tissue engineered cartilage application. Upon removal of the discs from the glutaraldehyde they were rinsed with several changes of deionized water and then allowed to soak in water overnight. They were then rinsed again and placed in 70% (v/v) isopropanol/water solution as a disinfectant prior to use for cell-seeding and bioreactor studies.

What is claimed is:

1. A graft comprising (1) a bioabsorbable filament having an exterior surface and a central lumen having an interior wall opening through the exterior surface, wherein the central lumen comprises a hydrophilic interior effective to wick the cells into the filament; and (2) cells capable of initiating hair follicle neogenesis comprising epidermal cells and dermal cells disposed within the lumen.

2. The graft of claim 1, wherein the dermal cells are obtained from skin, hair follicles, dermal papilla, or dermal sheath.

3. The graft of claim 1, wherein the dermal cells are an aggregated clump of dermal cells.

4. The graft of claim 1, wherein the epidermal cells are obtained from skin, hair follicles, inner hair root sheath, or outer hair root sheath.

5. The graft of claim 1, wherein the epidermal cells are adhered to the interior wall of the lumen.

6. The graft of claim 1, wherein the epidermal cells are adjacent to the interior wall of the lumen.

7. The graft of claim 1, wherein the interior wall of the lumen is smooth.

8. The graft of claim 1, wherein the interior wall of the lumen is porous.

9. The graft of claim 1, wherein the bioabsorbable filament is porous.

10. The graft of claim 1, wherein the interior wall of the lumen is coated with a bioabsorbable filler material.

11. The graft of claim 1, wherein the bioabsorbable filament is modified with a modifier selected from the group consisting of angiogenesis factors, growth factors, cell attachment binding site moieties, cell signaling molecules, proteins, glycoproteins, collagen, laminin, and fibronectin.

12. The graft of claim 11, wherein the cell attachment binding site moiety is a peptide comprising a cell attachment domain sequence.

13. The graft of claim 12, wherein the cell attachment domain sequence is Arg-Gly-Asp.

14. The graft of claim 1, wherein the epidermal and dermal cells are derived from different sources.

15. The graft of claim 1, wherein the epidermal cells and dermal cells are present in the graft in an amount and proportion sufficient to initiate hair follicle neogenesis.

16. The graft of claim 1, wherein filament comprises a first end that is closed.

17. The graft of claim 16, wherein the cells are concentrated at the first end.

18. The graft of claim 1, wherein the hydrophilic interior has a faster rate of bioabsorption or liquefaction than the exterior of the filament.

19. A graft comprising (1) a bioabsorbable filament having a central lumen having an interior wall; and (2) cells capable of initiating hair follicle neogenesis comprising epidermal cells and dermal cells, wherein the epidermal cells are adjacent to the interior wall of the lumen, and the dermal cells are located within the lumen.

* * * * *

UNITED STATES PATENT AND TRADEMARK OFFICE
CERTIFICATE OF CORRECTION

PATENT NO. : 7,597,885 B2
APPLICATION NO. : 10/810518
DATED : October 6, 2009
INVENTOR(S) : Thomas H. Barrows, Stephen A. Cochran and Bryan Marshall It is certified that error appears in the above-identified patent and that said Letters Patent is hereby corrected as shown below:

Claim 16, column 18, line 31, replace "wherein filament" with --wherein the filament--.
Claim 18, column 18, line 36, replace "bioabsorption or liquefaction than the exteroir" with --bioabsorption than the exterior--.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,597,885 B2  Page 1 of 1
APPLICATION NO. : 10/810518
DATED : October 6, 2009
INVENTOR(S) : Barrows et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this

Twenty-eighth Day of September, 2010

David J. Kappos
*Director of the United States Patent and Trademark Office*